United States Patent
Wachi et al.

(10) Patent No.: US 10,667,763 B2
(45) Date of Patent: Jun. 2, 2020

(54) PROCESSING DEVICE, METHOD, AND RECORDING MEDIUM FOR GRAPHICAL VISUALIZATION OF BIOLOGICAL INFORMATION

(71) Applicant: TANITA CORPORATION, Tokyo (JP)

(72) Inventors: Yuto Wachi, Tokyo (JP); Haruna Nakatani, Tokyo (JP); Toru Ichihashi, Tokyo (JP); Toshihide Murata, Tokyo (JP); Hiroshi Koi, Tokyo (JP); Akihiro Chaya, Tokyo (JP); Saki Kato, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 0 days.

(21) Appl. No.: 15/836,569

(22) Filed: Dec. 8, 2017

(65) Prior Publication Data
US 2018/0168517 A1 Jun. 21, 2018

(30) Foreign Application Priority Data

Dec. 16, 2016 (JP) .................................. 2016-244926

(51) Int. Cl.
*A61B 5/00* (2006.01)
*G16H 10/60* (2018.01)
(Continued)

(52) U.S. Cl.
CPC .............. *A61B 5/743* (2013.01); *A61B 5/053* (2013.01); *A61B 5/4023* (2013.01);
(Continued)

(58) Field of Classification Search
None
See application file for complete search history.

(56) References Cited

U.S. PATENT DOCUMENTS 5,598,359 A * 1/1997 Montag ................. G06T 11/001
434/2
2002/0007125 A1 * 1/2002 Hickey ................ A61B 5/0215
600/486

(Continued)

FOREIGN PATENT DOCUMENTS

EP 1393675 A1 3/2004
JP 2004-081621 A 3/2004

*Primary Examiner* — Xiao M Wu
*Assistant Examiner* — Steven Z Elbinger
(74) *Attorney, Agent, or Firm* — Studebaker & Brackett PC

(57) ABSTRACT

A biological information processing device includes a controller programmed to obtain biological information indicating a body condition, and associate different kinds of the biological information with respective specific graphical elements. Each of the respective specific graphical elements constitute a respective specific appearance of a graphical figure, with one of the respective specific graphical elements representing a surface count of a polyhedron which changes in relation to a numerical change in the biological information. The controller is further programmed to set value to the specific graphical element depending on degree of the biological information for at least one specific graphical element associated with the biological information obtained, and generate indicating data of a biological figure on the basis of the value set, the biological figure being an aggregate of the specific graphical elements.

19 Claims, 20 Drawing Sheets

(51) Int. Cl.
*G16H 15/00* (2018.01)
*A61B 5/053* (2006.01)
*G01G 19/50* (2006.01)

(52) U.S. Cl.
CPC .......... *A61B 5/4509* (2013.01); *A61B 5/4519* (2013.01); *A61B 5/4866* (2013.01); *A61B 5/4872* (2013.01); *A61B 5/4875* (2013.01); *A61B 5/7282* (2013.01); *G01G 19/50* (2013.01); *G16H 10/60* (2018.01); *G16H 15/00* (2018.01)

(56) References Cited

U.S. PATENT DOCUMENTS

| | | | | |
|---|---|---|---|---|
| 2004/0027350 A1* | 2/2004 | Kincaid | ................ | G06T 11/206 345/440 |
| 2004/0054298 A1* | 3/2004 | Masuo | ................ | A61B 5/0537 600/547 |
| 2004/0064071 A1* | 4/2004 | Kasahara | ............. | A61B 5/0537 600/595 |
| 2004/0254496 A1* | 12/2004 | Itagaki | ................ | A61B 5/0537 600/547 |
| 2008/0010065 A1* | 1/2008 | Bratt | .................... | G06K 9/6222 704/246 |
| 2008/0073128 A1* | 3/2008 | Umemoto | ........... | A61B 5/0537 177/5 |
| 2008/0214903 A1 | 9/2008 | Orbach | | |
| 2008/0270080 A1 | 10/2008 | Zong | | |
| 2010/0100392 A1* | 4/2010 | Rothman | ............... | G06Q 50/22 705/2 |
| 2011/0021936 A1* | 1/2011 | Luo | ........................ | A61B 5/044 600/523 |
| 2012/0239434 A1* | 9/2012 | Breslow | ................ | G16H 15/00 705/3 |
| 2015/0268831 A1* | 9/2015 | Sripada | ................ | G06F 3/0488 715/849 |
| 2018/0052088 A1* | 2/2018 | Sarkar | ............... | G01N 15/0227 |

* cited by examiner

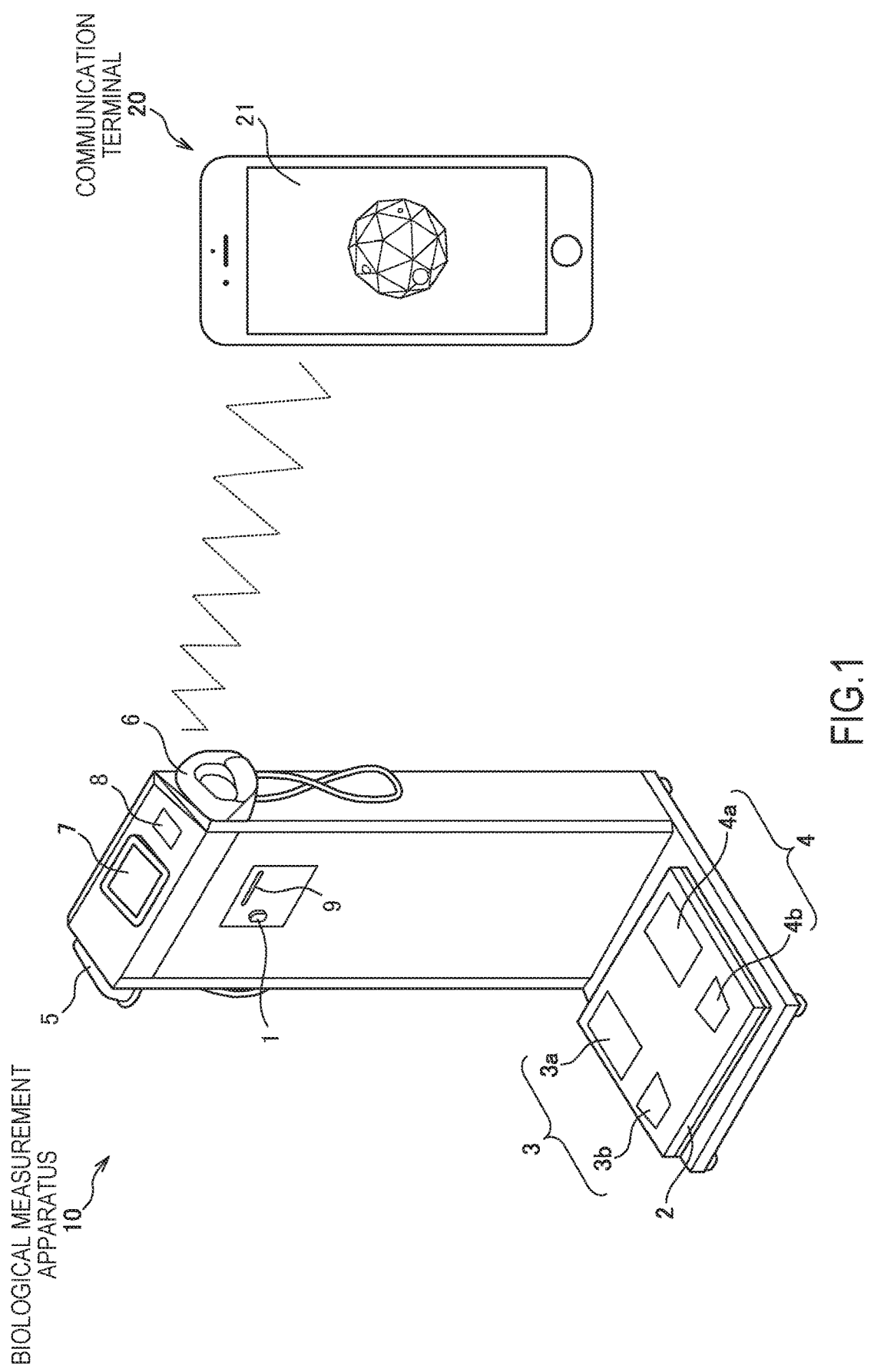

| FIRST FIGURE ELEMENT TABLE T1 | | SECOND FIGURE ELEMENT TABLE T2 | | THIRD FIGURE ELEMENT TABLE T3 | | FOURTH FIGURE ELEMENT TABLE T4 | |
|---|---|---|---|---|---|---|---|
| BIOLOGICAL INFORMATION | FIGURE ELEMENT | BIOLOGICAL INFORMATION | FIGURE ELEMENT | BIOLOGICAL INFORMATION | FIGURE ELEMENT | BIOLOGICAL INFORMATION | FIGURE ELEMENT |
| BASAL METABOLIC RATE Me | COLOR GRADATION | VISCERAL FAT LEVEL Fl | SPHERICAL BODY SIZE | MUSCLE MASS Mu | SURFACE COUNT | BODY BALANCE Ba | APEX VIBRATION WIDTH |
| $u_{LL} \leqq Me < u_1$ | $A_1$ | $v_{LL} \leqq Fl < v_1$ | $B_1$ | $w_{LL} \leqq Mu < w_1$ | $C_1$ | $x_{LL} \leqq Ba < x_1$ | $D_1$ |
| $u_1 \leqq Me < u_2$ | $A_2$ | $v_1 \leqq Fl < v_2$ | $B_2$ | $w_1 \leqq Mu < w_2$ | $C_2$ | $x_1 \leqq Ba < x_2$ | $D_2$ |
| ... | ... | ... | ... | ... | ... | ... | ... |
| $u_{n-1} \leqq Me < u_n$ | $A_{n-1}$ | $v_{n-1} \leqq Fl < v_n$ | $B_{n-1}$ | $w_{n-1} \leqq Mu < w_n$ | $C_{n-1}$ | $x_{n-1} \leqq Ba < x_n$ | $D_{n-1}$ |
| $u_n \leqq Me < u_{HL}$ | $A_n$ | $v_n \leqq Fl < v_{HL}$ | $B_n$ | $w_n \leqq Mu < w_{HL}$ | $C_n$ | $x_n \leqq Ba < x_{HL}$ | $D_n$ |

| | FIRST COMPONENT FIGURE TABLE T11 | | SECOND COMPONENT FIGURE TABLE T12 | | THIRD COMPONENT FIGURE TABLE T13 | | FOURTH COMPONENT FIGURE TABLE T14 | |
|---|---|---|---|---|---|---|---|---|
| | BODY CONFIGURATION INFORMATION | COMPONENT FIGURE | BODY CONFIGURATION INFORMATION | COMPONENT FIGURE | BODY CONFIGURATION INFORMATION | COMPONENT FIGURE | BODY CONFIGURATION INFORMATION | COMPONENT FIGURE |
| | FAT MASS F | CIRCLE COUNT | MUSCLE MASS Mu | SQUARE COUNT | BONE MASS Bo | ARROW COUNT | MOISTURE AMOUNT Mo | CLOUD SHAPE COUNT |
| | $q_{LL} \leq F < q_1$ | $E_1$ | $r_{LL} \leq Mu < r_1$ | $F_1$ | $s_{LL} \leq Bo < s_1$ | $G_1$ | $t_{LL} \leq Mo < t_1$ | $H_1$ |
| | $q_1 \leq F < q_2$ | $E_2$ | $r_1 \leq Mu < r_2$ | $F_2$ | $s_1 \leq Bo < s_2$ | $G_2$ | $t_1 \leq Mo < t_2$ | $H_2$ |
| | ... | ... | ... | ... | ... | ... | ... | ... |
| | $q_{m-1} \leq F < q_m$ | $E_{m-1}$ | $r_{m-1} \leq Mu < r_m$ | $F_{m-1}$ | $s_{m-1} \leq Bo < s_m$ | $G_{m-1}$ | $t_{m-1} \leq Mo < t_m$ | $H_{m-1}$ |
| | $q_m \leq F < q_{UL}$ | $E_m$ | $r_m \leq Mu < r_{UL}$ | $F_m$ | $s_m \leq Bo < s_{UL}$ | $G_m$ | $t_m \leq Mo < t_{UL}$ | $H_m$ |

203A

203B

T21

| FIRST VARIATION INDICATING TABLE | | |
|---|---|---|
| FAT MASS F | COMPONENT FIGURE | |
| FAT VARIATION AMOUNT Df | CIRCLE | |
| | DISCHARGE COUNT | ABSORB COUNT |
| $m_{-k+1} \leqq Df < m_{-k}$ | $I_{-k}$ | 0 |
| ⋮ | ⋮ | ⋮ |
| $m_{-2} \leqq Df < m_{-1}$ | $I_{-1}$ | 0 |
| $m_{-1} \leqq Df < m_{+1}$ | 0 | 0 |
| $m_{+1} \leqq Df < m_{+2}$ | 0 | $I_{+1}$ |
| ⋮ | ⋮ | ⋮ |
| $m_{+k} \leqq Df < m_{+k+1}$ | 0 | $I_{+k}$ |

T22

| SECOND VARIATION INDICATING TABLE | | |
|---|---|---|
| MUSCLE MASS Mu | COMPONENT FIGURE | |
| MUSCLE VARIATION AMOUNT Dmu | SQUARE | |
| | DISCHARGE COUNT | ABSORB COUNT |
| $n_{-k+1} \leqq Dmu < n_{-k}$ | $J_{-k}$ | 0 |
| ⋮ | ⋮ | ⋮ |
| $n_{-2} \leqq Dmu < n_{-1}$ | $J_{-1}$ | 0 |
| $n_{-1} \leqq Dmu < n_{+1}$ | 0 | 0 |
| $n_{+1} \leqq Dmu < n_{+2}$ | 0 | $J_{+1}$ |
| ⋮ | ⋮ | ⋮ |
| $n_{+k} \leqq Dmu < n_{+k+1}$ | 0 | $J_{+k}$ |

T23

| THIRD VARIATION INDICATING TABLE | | |
|---|---|---|
| BONE MASS Bo | COMPONENT FIGURE | |
| BONE VARIATION AMOUNT Dbo | ARROW | |
| | DISCHARGE COUNT | ABSORB COUNT |
| $o_{-k+1} \leqq Dbo < o_{-k}$ | $K_{-k}$ | 0 |
| ⋮ | ⋮ | ⋮ |
| $o_{-2} \leqq Dbo < o_{-1}$ | $K_{-1}$ | 0 |
| $o_{-1} \leqq Dbo < o_{+1}$ | 0 | 0 |
| $o_{+1} \leqq Dbo < o_{+2}$ | 0 | $K_{+1}$ |
| ⋮ | ⋮ | ⋮ |
| $o_{+k} \leqq Dbo < o_{+k+1}$ | 0 | $K_{+k}$ |

T24

| FOURTH VARIATION INDICATING TABLE | | |
|---|---|---|
| MOISTURE AMOUNT Mo | COMPONENT FIGURE | |
| MOISTURE VARIATION AMOUNT Dmo | CLOUD SHAPE | |
| | DISCHARGE COUNT | ABSORB COUNT |
| $p_{-k+1} \leqq Dmo < p_{-k}$ | $L_{-k}$ | 0 |
| ⋮ | ⋮ | ⋮ |
| $p_{-2} \leqq Dmo < p_{-1}$ | $L_{-1}$ | 0 |
| $p_{-1} \leqq Dmo < p_{+1}$ | 0 | 0 |
| $p_{+1} \leqq Dmo < p_{+2}$ | 0 | $L_{+1}$ |
| ⋮ | ⋮ | ⋮ |
| $p_{+k} \leqq Dmo < p_{+k+1}$ | 0 | $L_{+k}$ |

FIG.18

PROCESSING DEVICE, METHOD, AND RECORDING MEDIUM FOR GRAPHICAL VISUALIZATION OF BIOLOGICAL INFORMATION

TECHNICAL FIELD

The present invention relates to biological information processing, and relates to a biological information processing device that converts biological information into data indicated on a display, a biological information processing method, and a recording medium.

BACKGROUND ART

As an apparatus for measuring biological information, there has been proposed an apparatus that uses measured biological impedances to obtain a body fat ratio, a BMI (Body Mass Index), and distributions of fat and muscle and graphically displays the numerical values (JP2004-081621A).

SUMMARY OF INVENTION

The above-described apparatus only indicates the numerical values of the biological information such as the body fat ratio and the BMI as it is, and does not provide a measured person with the indication providing information specific to the person himself/herself except the specific numerical values. Then, it has been a problem that the measured person is not so interested in measurement of his/her biological information.

The present invention has been made in view of the above-described problem, and it is an object of the present invention to provide a biological information processing device that arouses interest in measurement results of the biological information, a biological information processing method, and a recording medium.

According to an aspect of the present invention, the biological information processing device includes a controller programmed to obtain biological information indicating a body condition, and associate different kinds of the biological information with respective specific graphical elements. Each of the specific graphical elements is same kind of element that constitutes an appearance of a graphical figure. The controller is further programmed to set value to the specific graphical element depending on degree of the biological information for the at least one specific graphical element associated with the obtained biological information, and generate indicating data of a biological figure that is an aggregate of the specific graphical elements on the basis of the set value.

With the aspect, a variation of one kind of the biological information ensures totally changing the appearance of the biological figure, thus easily indicating features unique to the biological figure indicated to each person corresponding to numerical values of the biological information. Accordingly, the measured person is easily provided with information specific to the person himself/herself as a measurement result, thus ensuring the measured person to be interested in the measurement result of the biological information.

BRIEF DESCRIPTION OF DRAWINGS

FIG. 1 is a drawing illustrating appearances of a biological measurement apparatus that includes a biological information processing device and a communication terminal in a first embodiment of the present invention.

FIG. 6 is a drawing illustrating an exemplary figure conversion table for changing an appearance of the biological figure by using one kind of biological information.

FIG. 14 is a drawing illustrating an exemplary component figure table associating mutually different body configuration informations in the biological informations with respective component figures to conceive the body configuration informations.

FIG. 18 is a drawing illustrating a correspondence table that associates a variation amount of the body configuration information measured in time series with a variation amount of the component figure.

DESCRIPTION OF EMBODIMENTS

Figure 2A:
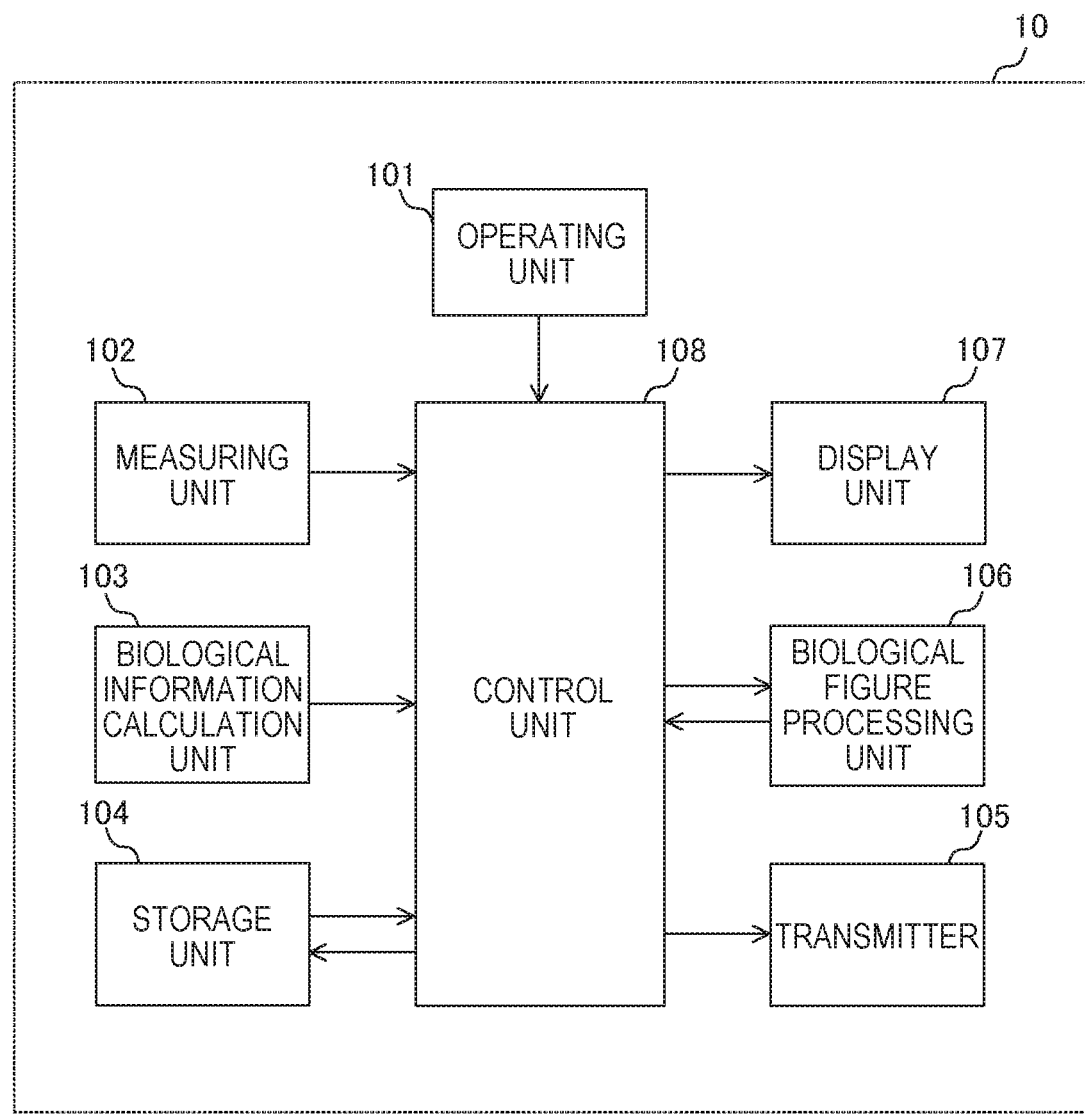
FIG. 2A is a block diagram illustrating an exemplary function composition of the biological measurement apparatus according to the embodiment.

The following describes embodiments of the present invention by referring to the attached drawings.

First Embodiment

FIG. 1 is a drawing illustrating appearances of a biological measurement apparatus 10 and a communication terminal 20 in a first embodiment of the present invention.

The biological measurement apparatus 10 is an apparatus that measures biological information indicating a health condition of a body of a measured person. The biological information of this embodiment includes biological information obtained by using the biological measurement apparatus 10 to directly measure the person to be measured, biological information obtained by input operations by the measured person, and biological information obtained by calculating the biological informations with a predetermined regression formula.

The biological measurement apparatus 10 includes a power switch 1, a scale 2 that measures a weight, electrode portions 3 and 4 that measure biological impedances of both feet, electrode portions 5 and 6 that measure biological impedances of both hands, a display operating device 7, a communication device 8, and a print device 9.

On the scale 2, the electrode portions 3 and 4 are disposed such that respective bottoms of both feet contact placing surfaces for placing both feet of the measured person. The electrode portions 3 and 4 are constituted of electrodes 3a and 4a that provide currents to left and right feet of the measured person respectively, and electrodes 3b and 4b that measure voltages on both feet. The electrode portions 5 and 6 also are each constituted of first electrodes that provide currents to left and right hands of the measured person respectively, and second electrodes that measure voltages on both hands.

The display operating device 7 includes an operating unit 101 (see FIG. 2) for inputting basic biological information such as a height, an age and a gender of the measured person, and a display unit 107 (see FIG. 2) that displays measurement results to the measured person. The display operating device 7 is achieved by, for example, a touchscreen-type liquid crystal display unit.

The communication device 8 communicates with the communication terminal 20. For example, the communication device 8 communicates using short-range wireless communication, a mobile phone network, and similar network. The communication device 8 of this embodiment transmits the biological information obtained by the biological measurement apparatus 10 to the communication terminal 20.

The communication terminal 20 is a mobile terminal that uses the short-range wireless communication, the mobile phone network, and similar network for communicating. The communication terminal 20 of this embodiment receives the biological information transmitted from the communication device 8, and displays the measurement result on a screen 21 on the basis of the received biological information.

FIG. 2A is a block diagram illustrating a main function composition of the biological measurement apparatus 10 according to the embodiment.

The biological measurement apparatus 10 includes the operating unit 101, a measuring unit 102, a biological information calculation unit 103, a storage unit 104, a transmitter 105, a biological figure processing unit 106, the display unit 107, and a control unit 108.

The operating unit 101 accepts an operation for switching the power switch 1 to ON or OFF. The operating unit 101 accepts the basic biological information input by the operation of the measured person. The information is input to the operating unit 101 by, for example, a touch sensor, or a button and a dial.

The measuring unit 102 uses the scale 2 to measure the weight of the measured person. The measuring unit 102 further uses the electrode portions 3 to 6 to measure the biological impedances of the measured person.

The biological information calculation unit 103 applies the weight and the biological impedances measured by the measuring unit 102 and the basic biological information such as the height, the age, and the gender input to the operating unit 101 to the predetermined regression formula, so as to operate the other biological information. The other biological information includes biological indexes such as fat ratios of the whole body and each region of the whole body, a fat mass, a fat-free mass, a muscle mass, a visceral fat mass, a visceral fat level, a visceral fat area, a subcutaneous fat mass, a basal metabolic rate, a bone mass, a body moisture content, a water content, a BMI (Body Mass Index), an intracellular fluid volume, an extracellular fluid volume, and a body balance. In this embodiment, one biological information is assigned to each of the biological indexes.

The storage unit 104 is constituted of a non-volatile memory (ROM; Read Only Memory), a volatile memory (RAM; Random Access Memory), and similar memory. The storage unit 104 stores a control program that controls operations of the biological measurement apparatus 10. The storage unit 104 is a storing medium that stores programs to realize functions of this embodiment.

The storage unit 104 stores the basic biological information input to the operating unit 101, the weight and the biological impedances measured by the measuring unit 102, and the calculation result calculated by using the predetermined regression formula in the biological information calculation unit 103 as the biological information associating with time information. The storage unit 104 further stores a figure conversion table converting the biological information into a biological figure indicating the health condition of the measured person.

The transmitter 105 transmits the biological information stored in the storage unit 104 to the communication terminal 20 via the communication device 8 to inform the health condition of the measured person. The biological information transmitted to the communication terminal 20 includes, for example, the weight, the height, the fat ratios of the whole body and each region of the whole body, the fat mass, the fat-free mass, the muscle mass, the visceral fat level, the subcutaneous fat mass, the basal metabolic rate, the bone mass, the body moisture content, and the BMI.

The biological figure processing unit 106 obtains the biological information for indicating on the display unit 107 to generate a biological figure having an appearance different for each numerical value of the obtained biological information with reference to the figure conversion table stored in the storage unit 104. The biological figure processing unit 106 generates figure indicating data for indicating the generated biological figure on the display unit 107. It should be noted that the biological figure processing unit 106 corresponds to the biological information processing device.

The display unit 107 is display means that displays the biological information stored in the storage unit 104, the biological figure, and similar information.

The control unit 108 is constituted of a central processing unit (CPU; Central Processing Unit), an input interface, and a bus that couples the CPU to the input interface. The control unit 108 reads the control program stored in the storage unit 104 to cause the central processing unit to execute the program, so as to control each unit of the biological measurement apparatus 10 via the input interface.

The control unit 108 of this embodiment controls each of the operating unit 101, the measuring unit 102, the biological information calculation unit 103, the storage unit 104, the transmitter 105, the biological figure processing unit 106, and the display unit 107. The control unit 108 of this embodiment obtains the biological information from the operating unit 101, the measuring unit 102, and the biological information calculation unit 103 to change the appearance of the biological figure corresponding to the numerical values of the biological information.

Figure 2B:
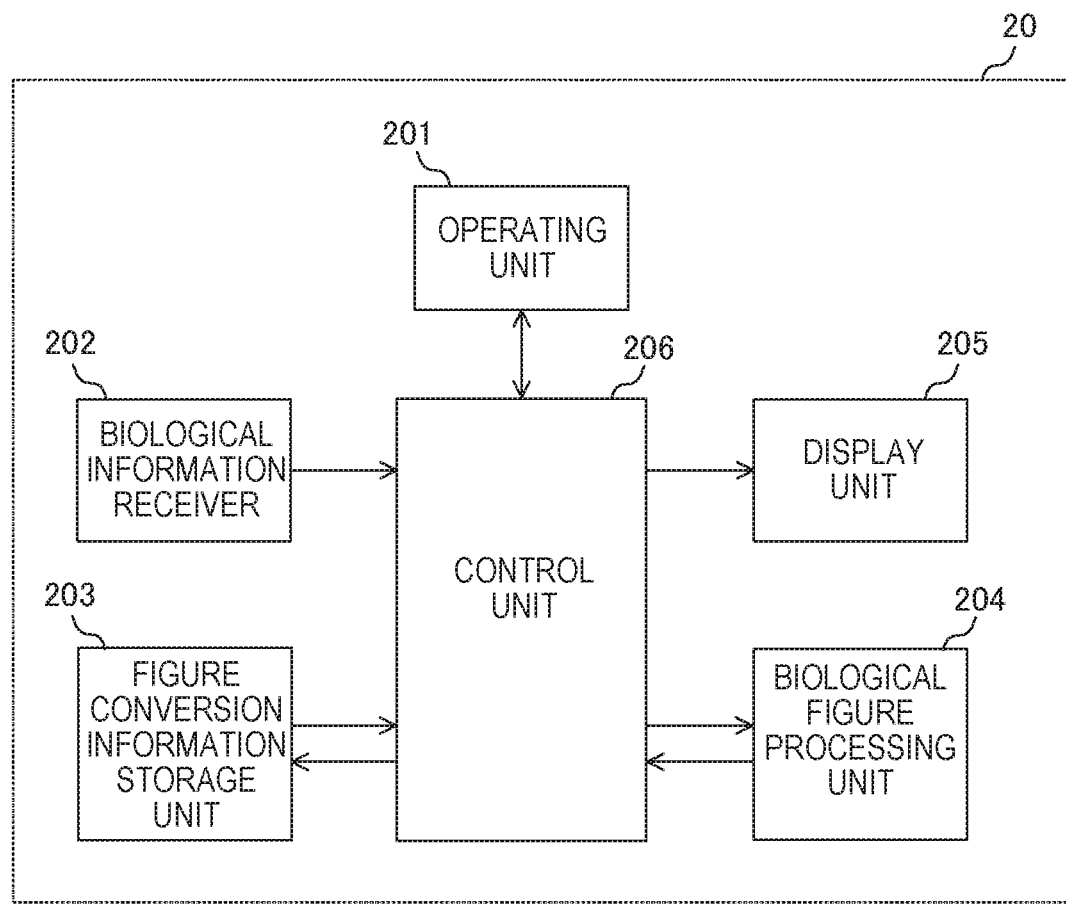
FIG. 2B is a block diagram illustrating an exemplary function composition of the communication terminal according to the embodiment.

FIG. 2B is a block diagram illustrating a main function composition of the communication terminal 20 according to the embodiment.

The communication terminal 20 displays the biological figure on the basis of the biological information transmitted from the transmitter 105. The communication terminal 20 includes an operating unit 201, a biological information receiver 202, a figure conversion information storage unit 203, a biological figure processing unit 204, a display unit 205, and a control unit 206.

The operating unit 201 accepts input operations by a user. The operating unit 201 of this embodiment accepts, for example, an operation instructing a reception of the biological information from the biological measurement apparatus 10.

The biological information receiver 202 communicates with the transmitter 105 of the biological measurement apparatus 10 to receive the biological information transmitted from the transmitter 105.

The figure conversion information storage unit 203 is constituted of a non-volatile memory (ROM), a volatile memory (RAM), and similar memory. The figure conversion information storage unit 203 stores a control program that controls operations of the communication terminal 20. The figure conversion information storage unit 203 is a storing medium that stores programs to realize functions of this embodiment.

The figure conversion information storage unit 203 of this embodiment stores the received biological information and stores the figure conversion table similarly to the storage unit 104 of the biological measurement apparatus 10. The figure conversion table is preliminarily stored in the figure conversion information storage unit 203. The figure conversion table may be received from the biological measurement apparatus 10 with the biological information.

The biological figure processing unit 204 has a configuration similar to the biological figure processing unit 106 of the biological measurement apparatus 10. In this embodiment, the biological figure processing unit 204 obtains all or a part of the biological information stored in the figure conversion information storage unit 203, and refers to the figure conversion table for each of the biological informations so as to generate the figure indicating data. It should be noted that the biological figure processing unit 204 corresponds to the biological information processing device.

The display unit 205 is display means that displays the biological figure generated on the basis of the figure indicating data and a plurality of the numerical values of the biological information stored in the figure conversion information storage unit 203 in a predetermined format.

The control unit 206 is constituted of a central processing unit (CPU), an input interface, and a bus that couples the CPU to the input interface. The control unit 206 reads the control program stored in the figure conversion information storage unit 203 to cause the central processing unit to execute the program, so as to control each unit of the communication terminal 20 via the input interface.

The control unit 206 of this embodiment controls each of the operating unit 201, the biological information receiver 202, the figure conversion information storage unit 203, the biological figure processing unit 204, and the display unit 205. The control unit 206 of this embodiment causes the display unit 205 to indicate the biological figure reflecting numerical values of the four biological informations on the appearance on the basis of the figure indicating data generated by the biological figure processing unit 204.

Figure 3:
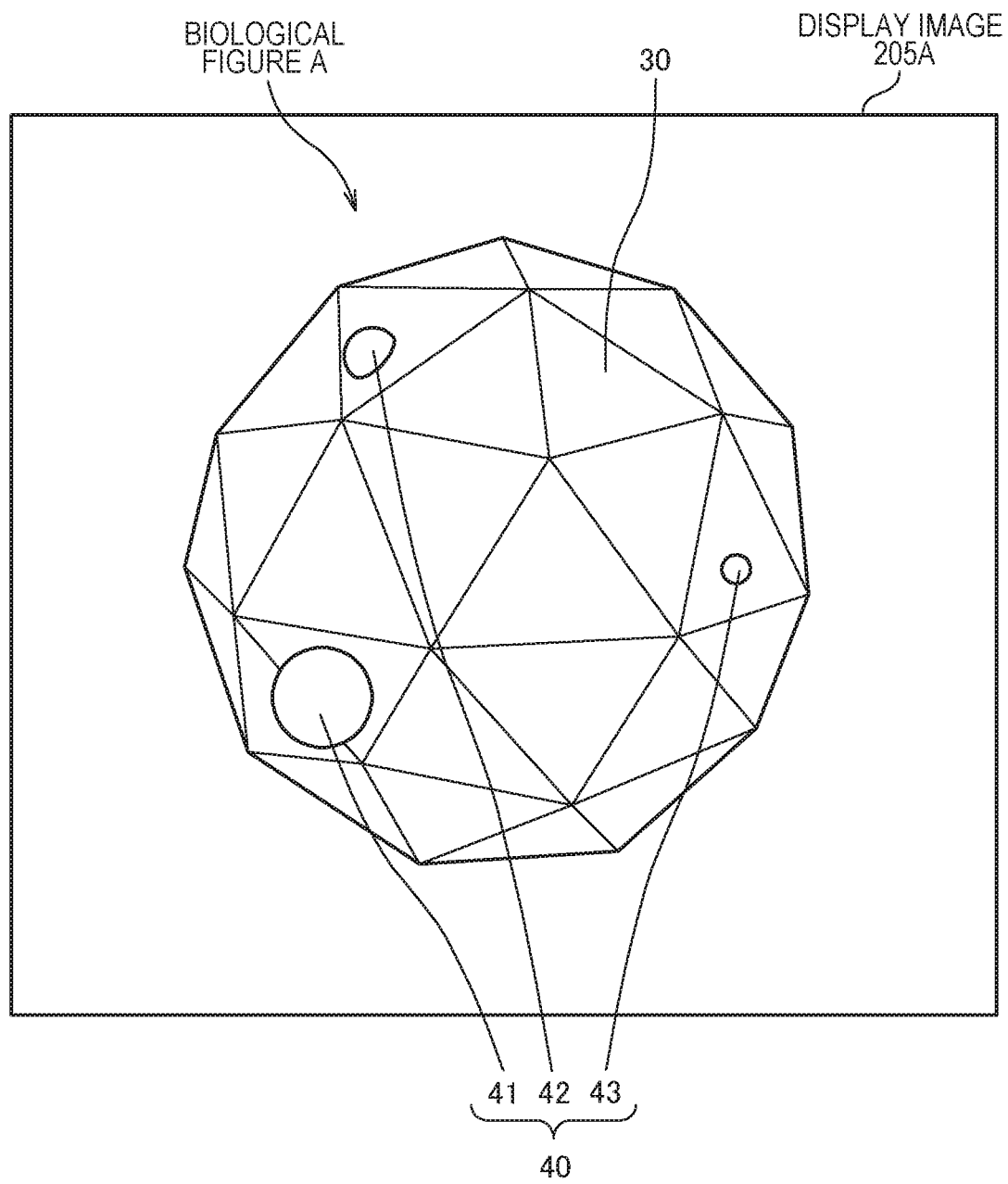
FIG. 3 is a drawing illustrating an exemplary display image generated by a biological figure processing according to the embodiment.

FIG. 3 is a drawing illustrating an exemplary display image of the biological figure indicated on the display unit 205.

A display image 205A displays a biological figure A, and the biological figure A is constituted of a polyhedron 30 and a plurality of spherical bodies 41 to 43 emitted from a center (a center of gravity) of the polyhedron 30.

In this example, the polyhedron 30 is colored in blue, and the spherical bodies 41 to 43 are each colored in white. A most part of the spherical body 41 is exposed from the polyhedron 30, a half of the spherical body 42 is exposed from the polyhedron 30, and a distal end portion of the spherical body 43 is exposed from the polyhedron 30. Apexes constituting the polyhedron 30 each vibrate in a predetermined cycle in a direction to vary the distance from the center of the polyhedron 30.

On the biological figure A, the color of the polyhedron 30 varies corresponding to the numerical value of first biological information, and sizes of the spherical bodies 41 to 43 vary corresponding to the numerical values of second biological information. The number of the surfaces of the polyhedron 30 increases and decreases corresponding to the numerical value of third biological information, and vibration widths of the respective apexes of the polyhedron 30 vary corresponding to the numerical values of fourth biological information.

Thus, in this embodiment, specific graphical elements constituting the appearance of the biological figure A, for example, a color gradation of the polyhedron 30, a group of the surfaces, a group of the apexes, and a plurality of spherical bodies 40, each vary corresponding to the numerical values of one biological information different from one another. Each of the specific graphical elements is same kind (identical kind) of elements constituting the appearance of the biological figure A. Thus, since the appearance and an outline of the biological figure A vary by each numerical value of the biological information, the display unit 205 of the communication terminal 20 displays the biological figure A unique to only the measured person. This ensures the measured person to be interested in the measurement of the biological information.

Figure 4:
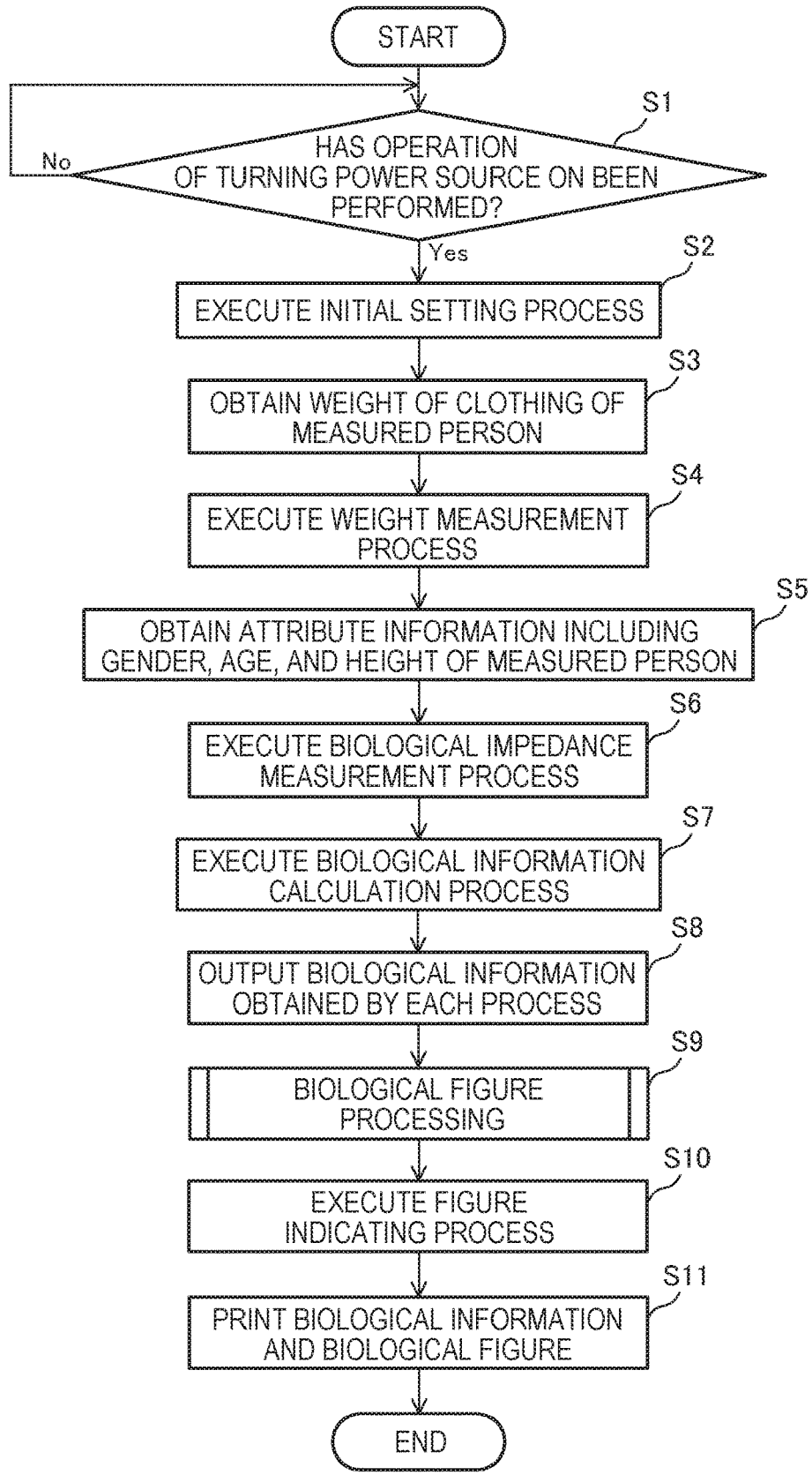
FIG. 4 is a flowchart indicating an exemplary processing method of the biological information by the biological measurement apparatus.

FIG. 4 is a flowchart indicating an exemplary procedure of a control method by the biological measurement apparatus 10 according to the embodiment.

First, when the power switch 1 of the biological measurement apparatus 10 is set to ON, in Step S1, the control unit 108 determines that an operation of turning the power source ON has been performed.

In Step S2, the control unit 108 initializes each of the power switch 1, the scale 2, the electrode portions 3 to 6, the display operating device 7, the communication device 8, and the print device 9.

In Step S3, the control unit 108 controls the display unit 107 to indicate a message requesting an input of a weight of clothing on the display operating device 7, and obtains the weight of the clothing input by the measured person from the operating unit 101.

In Step S4, the control unit 108 controls the measuring unit 102 to measure a weight of the measured person. Then, the control unit 108 controls the display unit 107 to indicate a numerical value obtained by subtracting the weight of the clothing from the measured value on the display operating device 7 as the weight of the measured person. The control unit 108 records the weight in the storage unit 104 as the biological information.

In Step S5, the control unit 108 controls the display unit 107 to indicate a message requesting an input of the basic biological information such as the gender, the age, and the height of the measured person on the display operating device 7, and obtains the basic biological information input by the measured person from the operating unit 101. The control unit 108 records the basic biological information of the measured person in the storage unit 104 as the biological information.

It should be noted that the biological measurement apparatus 10 may include an imaging device such that the imaging device takes an image of a face of the measured person, a general face-recognition processing is performed on the taken face image data, and the gender, the age, the height, and similar factor of the measured person obtained by the processing are used as the basic biological information.

In Step S6, the control unit 108 controls the measuring unit 102 to supply an alternating current from the electrode 3a to the electrode 4a, and detects a voltage between the electrode 3b and the electrode 4b in this state. Then, the measuring unit 102 calculates the biological impedances of the right foot and the left foot on the basis of the supplied current value and the detected voltage value. Similarly, the measuring unit 102 supplies an alternating current from the first electrode in the electrode portion 5 to the first electrode in the electrode portion 6, and detects a voltage between the second electrodes in the electrode portions 5 and 6 in this state. Then, the measuring unit 102 calculates the biological impedances of the right hand and the left hand on the basis of the supplied current value and the detected voltage value.

Thus, the measuring unit 102 calculates the biological impedance of each region of the right foot, the left foot, the right hand, and the left hand, and the whole body. The control unit 108 records the calculated biological impedances of the whole body and each region in the storage unit 104.

In Step S7, the control unit 108 uses the biological information calculation unit 103 to apply the basic biological information such as the weight, the biological impedances of the whole body and each region, the height, the age, and the gender, to the predetermined regression formula, so as to operate the biological information indicated on the display unit 107.

The biological information calculation unit 103 according to the embodiment calculates the basal metabolic rate, the muscle mass of the whole body, the visceral fat level, the body balance indicating a degree of collapse of a balance between right and left of the body, and similar factor as the biological information. The biological information calculation unit 103 calculates the body balance on the basis of a difference between the muscle mass on the left side and the muscle mass on the right side in the body, or a ratio of the muscle masses. For example, the biological information calculation unit 103 calculates the body balance by dividing a value obtained by subtracting the muscle mass of the left arm and the left foot from the muscle mass of the right arm and the right foot by an average value of the muscle mass of the right foot and the muscle mass of the left foot. The control unit 108 records the calculation result calculated by the biological information calculation unit 103 in the storage unit 104 as the biological information.

In Step S8, the control unit 108 controls the display unit 107 to indicate the whole or a part of the biological information stored in the storage unit 104 in association with time information on the display operating device 7. The control unit 108 displays a message querying whether to transmit the measurement result of this time to the communication terminal 20. Then, when the control unit 108 accepts the input requesting to transmit the measurement result from the operating unit 101, the control unit 108 controls the transmitter 105 to transmit the biological information associated with the time information from the communication device 8 to the communication terminal 20.

In Step S9, the control unit 108 uses the biological figure processing unit 106 to generate the figure indicating data constituting the biological figure A as illustrated in FIG. 3 on the basis of the biological information stored in the storage unit 104 and the above-described figure conversion table. This process will be described later in detail with reference to FIG. 5 to FIG. 12.

In Step S10, the control unit 108 controls the display unit 107 to indicate the biological figure generated on the basis of the figure indicating data on the display operating device 7.

In Step S11, the control unit 108 controls the print device 9 to print evaluation data indicating the numerical values of the biological information and the biological figure. Then, a sequence of the processes of the control method by the biological measurement apparatus 10 terminates.

Figure 5:
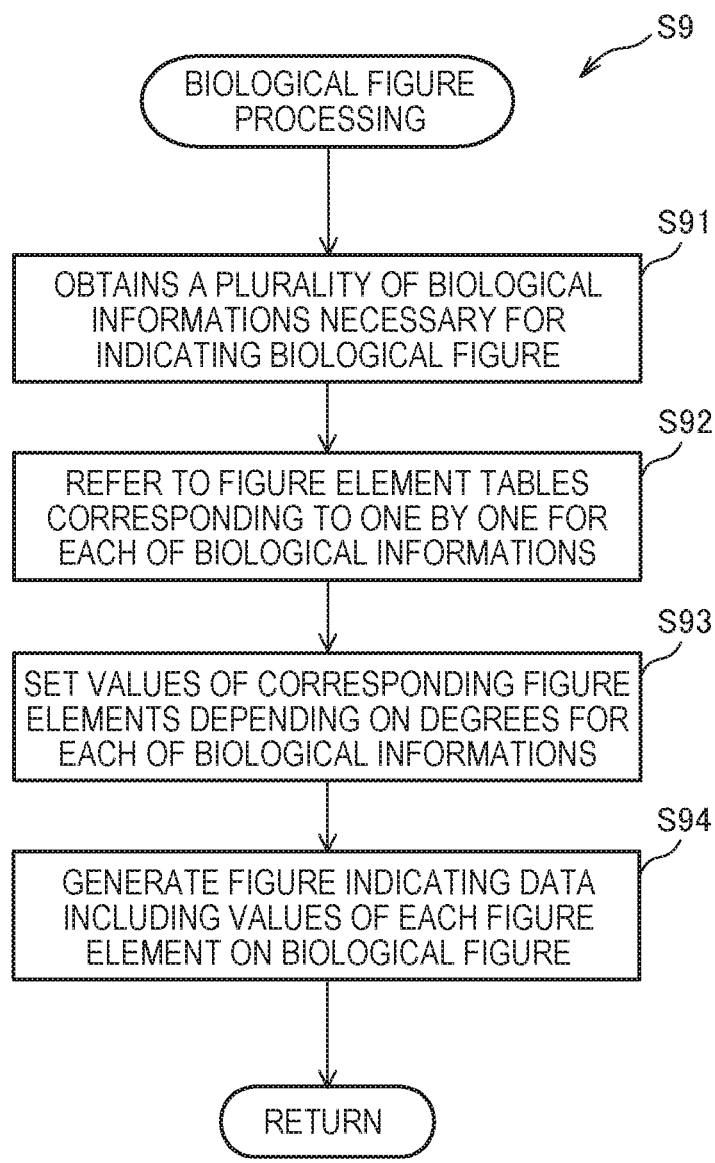
FIG. 5 is a flowchart indicating an exemplary procedure of the biological figure processing.

FIG. 5 is a flowchart indicating an exemplary procedure of the biological figure processing executed in Step S9.

In Step S91, the biological figure processing unit 106 obtains a plurality of biological informations necessary for indicating the biological figure. That is, the biological figure processing unit 106 constitutes obtaining means obtaining the biological information indicating a body condition. The biological figure processing unit 106 of this embodiment extracts the basal metabolic rate, the visceral fat level, the muscle mass, and the body balance as four biological informations among the biological informations stored in the storage unit 104.

In the above-described biological informations, the basal metabolic rate correlates with the fat-free mass, the weight, and the age. The visceral fat level is a fat level around internal organs and correlates with the fat mass, the height, and the age. The muscle mass is a mass of muscle composition including skeletal muscle and moisture, and correlates with the fat-free mass and a bone mineral content. The body balance is a biological index evaluating a balance of the body by a difference of the muscle mass between the right and left arms and feet in the body.

In Step S92, the biological figure processing unit 106 obtains the figure conversion table, where figure element tables and the biological information are associated in one-to-one, for constituting the appearance of the biological figure from the storage unit 104. Then, the biological figure processing unit 106 refers to the figure element tables corresponding to the respective biological informations obtained in Step S91 in the figure conversion table. That is, the biological figure processing unit 106 constitutes associating means that associates the figure elements constituting the appearance of the biological figure with the respective biological informations different from one another. The figure conversion table will be described later with reference to the next drawing.

In Step S93, the biological figure processing unit 106 changes a value of the figure element associated with one kind of the biological information corresponding to the numerical values of the biological information by each of the biological informations. That is, the biological figure processing unit 106 constitutes setting means that sets the mutually different values to the figure element associated with the biological information depending on the degrees of the biological informations.

In Step S94, the biological figure processing unit 106 generates the figure indicating data including the values of the figure elements corresponding to the respective four biological informations. That is, the biological figure processing unit 106 constitutes generating means that generates indicating data of the biological figure constituted of the figure elements on the basis of the values set to the figure elements. Then, a sequence of the processes of the biological figure processing terminates.

It should be noted that the biological figure processing executed in Step S9 is similarly performed in the biological figure processing unit 204 of the communication terminal 20. That is, the storage unit 104 and the figure conversion information storage unit 203 store programs configured to execute the biological figure processing by the computer. While this embodiment has described the example where the biological measurement apparatus 10 executes the biological figure processing, a computer other than the communication terminal 20, for example, an external server coupled to the communication terminal 20 via the mobile phone network, may execute the biological figure processing in Step S9.

For example, the biological measurement apparatus 10 is coupled to a microcomputer that includes a central processing unit (CPU) in which the biological figure processing is programed and a storage device in which the figure conversion table is stored. When the microcomputer receives the biological information measured by the biological measurement apparatus 10, the microcomputer refers to the figure conversion table to generate the figure indicating data of the biological figure on the basis of the numerical values of the biological information, and transmits the generated figure indicating data to the biological measurement apparatus 10. Thus, the other microcomputer may be configured to execute the biological figure processing.

FIG. 6 is a conceptual drawing illustrating an exemplary figure conversion table 104A stored in the storage unit 104. The figure conversion table 104A includes figure element tables T1 to T4 corresponding to the four biological informations.

In a first figure element table T1, a basal metabolic rate Me as one kind of the biological information is associated with a gradation of the color of the polyhedron constituting the appearance of the biological figure. In a variation range from a lower limit value $u_{LL}$ to an upper limit value $u_{HL}$ of the basal metabolic rate Me, every time that the numerical value of the basal metabolic rate Me exceeds separates $u_1$ to $u_n$ in phases, the color gradations $A_1$ to $A_n$ monotonously increase or decrease. A step number n is a positive number, and as the step number n increases, the color of the polyhedron continuously varies. The step number n is set to be, for example, 256.

In a second figure element table T2, a visceral fat level Fl as the biological information is associated with a size of the spherical body constituting the appearance of the biological figure. In a variation range from a lower limit value $v_{LL}$ to an upper limit value vim of the visceral fat level Fl, every time that the numerical value of the visceral fat level Fl exceeds separates $v_1$ to $v_n$ in phases, the spherical body sizes $B_1$ to $B_n$ monotonously increase or decrease.

In a third figure element table T3, a muscle mass Mu as the biological information is associated with the number of surfaces of the polyhedron constituting the appearance of the biological figure. In a variation range from a lower limit value $w_{LL}$ to an upper limit value $w_{HL}$ of the muscle mass Mu, every time that the numerical value of the muscle mass Mu exceeds separates $w_1$ to $w_n$ in phases, the surface counts $C_1$ to $C_n$ monotonously increase or decrease.

In a fourth figure element table T4, a body balance Ba as the biological information is associated with vibration widths of the respective apexes constituting the appearance of the biological figure. In a variation range from a lower limit value $x_{LL}$ to an upper limit value $x_{HL}$ of the body balance Ba, every time that the numerical value of the body balance Ba exceeds separates $x_1$ to $x_n$ in phases, the apex vibration widths $D_1$ to $D_n$ monotonously increase or decrease.

Thus, the above-described figure conversion table 104A is stored in the storage unit 104. That is, the storage unit 104 constitutes storage means that stores the figure element tables T1 to T4 where the numerical values of the biological information are associated with the values set to the figure element for each of the biological informations.

Then, after obtaining the biological information, the biological figure processing unit 106 refers to the plurality of the figure element tables T1 to T4 stored in the storage unit 104, and specifies (selects) the figure element table corresponding to the obtained biological information in the tables. Then, the biological figure processing unit 106 sets the values associated with the numerical values of the obtained biological information to the figure element necessary for generating figure indicating data on the basis of the specified figure element table. Thus, the biological figure processing unit 106 uses the figure conversion table 104A stored in the storage unit 104 to generate the figure indicating data, thus complexly varies the appearance of one biological figure corresponding to the numerical values of four biological informations. Then, the biological figure unique to only the measured person is easily generated.

Figure 7:
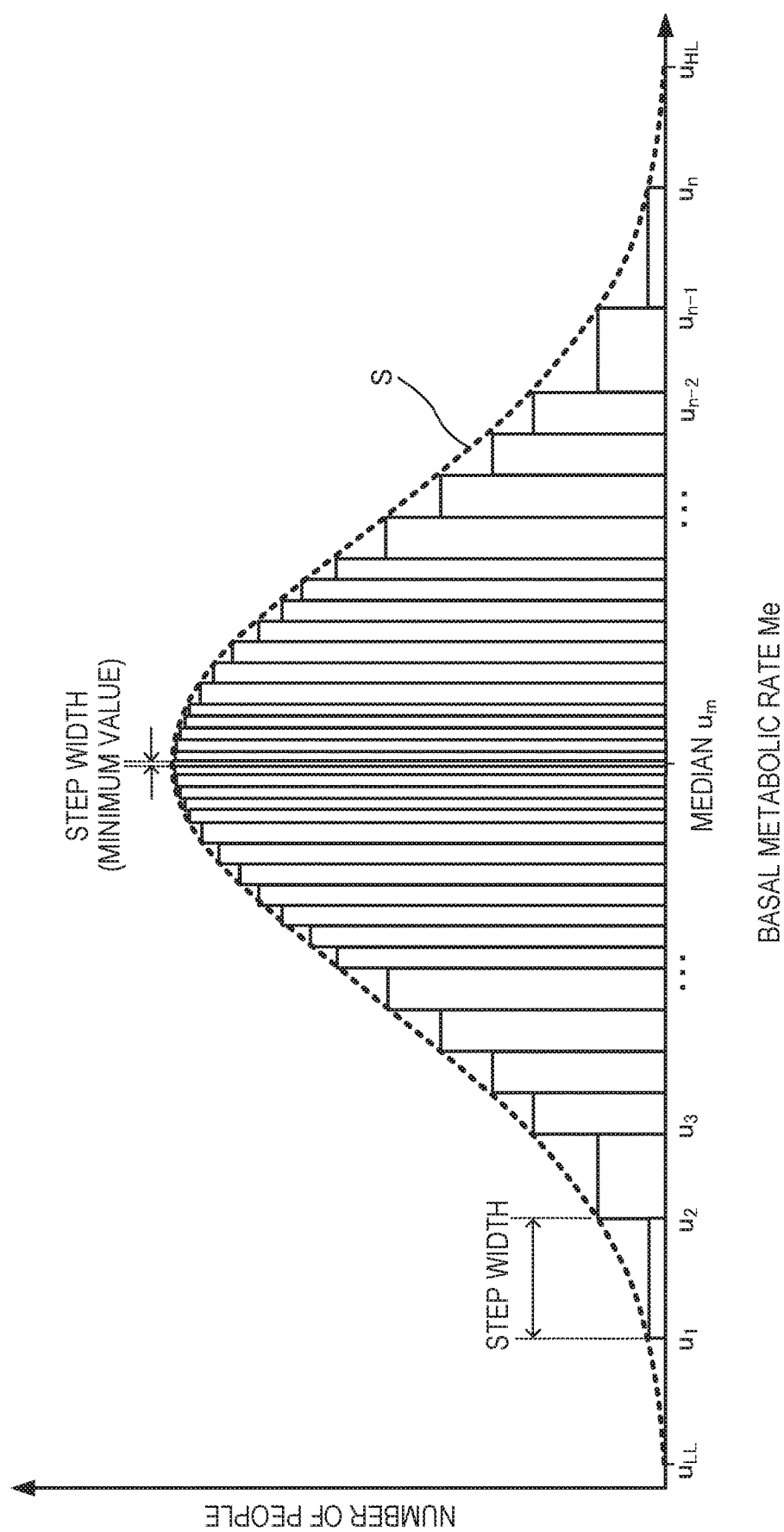
FIG. 7 is a drawing describing an exemplary setting of a step width for changing the biological figure in phases on the basis of statistical data on the biological information.

FIG. 7 is a drawing illustrating an exemplary setting method of the separates $u_1$ to $u_n$ in the first figure element table T1. FIG. 7 indicates a distribution of the number of people to the numerical values of the biological information, and a horizontal axis indicates each section (each region) of the basal metabolic rate Me and a vertical axis indicates the number of people in each section. A normal distribution curve S illustrated in FIG. 7 is obtained by an operation based on a lower limit value, a median, and an upper limit value extracted from statistical data on the basal metabolic rate Me.

As illustrated in FIG. 7, as distribution frequency of the normal distribution curve S increases (as approaching the median), the step width indicating a range of the biological information is set to a small value, and as the distribution frequency decreases (as approaching the upper limit value or the lower limit value), the step width is set to a large value.

For example, the step width of each section is set such that a product of the step width and the number of people is a constant value.

Thus, as the numerical value of the basal metabolic rate Me as the biological information approaches the median of the distribution of the number of people corresponding to the degree of the biological information, the step width is set to a small value. This provides the measured person whose basal metabolic rate Me is near the median with the biological figures having different appearances due to a slight difference of the basal metabolic rate Me compared with the case where the step widths of the respective sections are set to an identical value.

That is, as the numerical value of the biological information approaches a specific value, the variation amount set to the figure element to the variation amount of the numerical value of the biological information is increased, thus the degree of the variation of the appearance of the biological figure increases. This ensures providing the measured person with the unique biological figure different for each person. It should be noted that, in the second figure element table T2, the third figure element table T3, and the fourth figure element table T4, the respective separates ($v_1$ to $v_n$, $w_1$ to $w_n$, and $x_1$ to $x_n$) are set by similar methods.

In this embodiment, a description has been given of the example where the median of the distribution of the number of people in each region of the biological information is used as a criterion for changing the above-described step width. However, a statistic such as an average value, a mode, a deviation, and a standard deviation may be used instead of the median. Even the use of such other statistic ensures estimating a section where a numerical value of the biological information easily occurs frequently, thus decreasing a situation where an identical biological figure is assigned to many persons to be measured.

Next, a description will be given of a method for changing the appearance of the biological figure for each figure element according to the embodiment with reference to FIG. 8 to FIG. 11.

Figure 8:
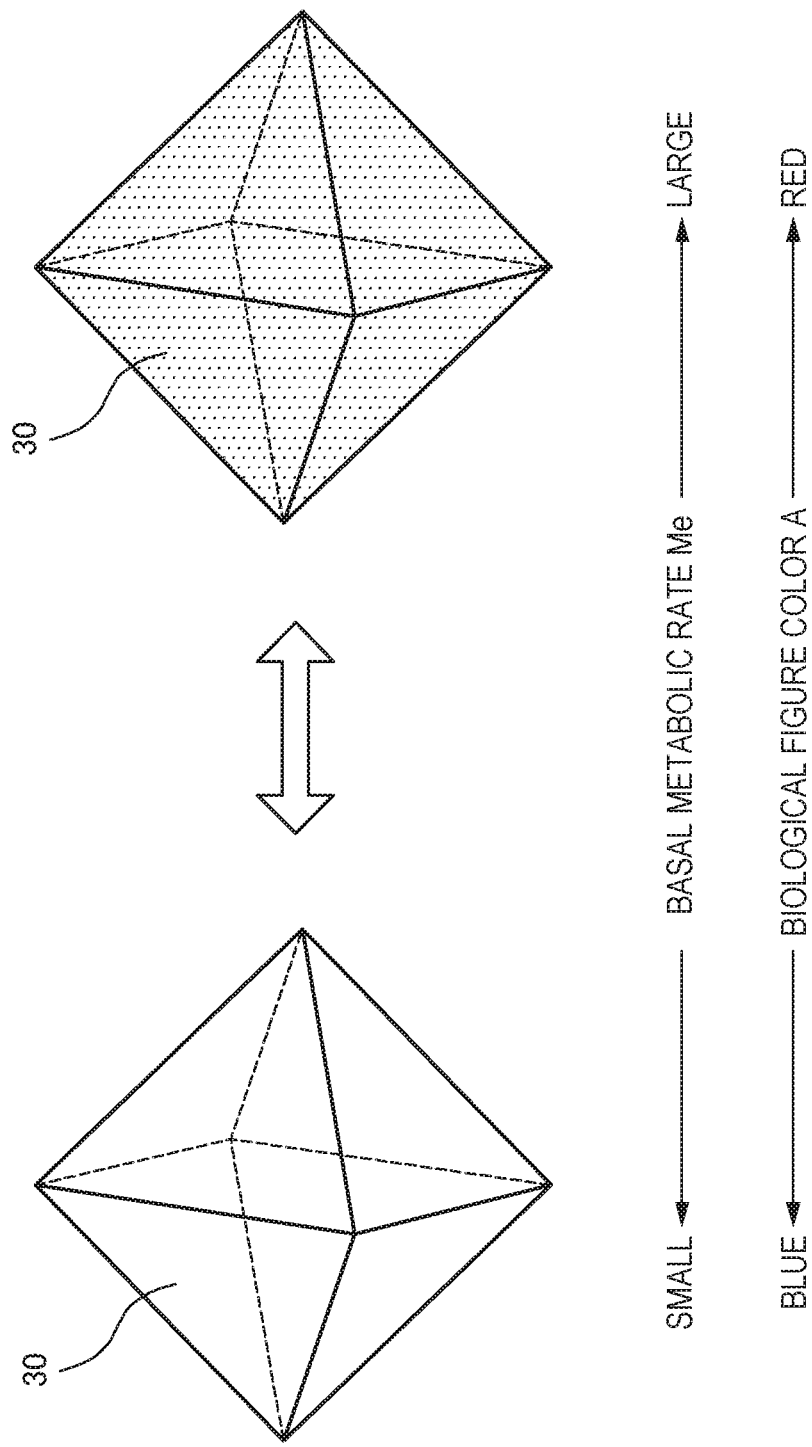
FIG. 8 is a drawing illustrating a relation between a basal metabolic rate as the biological information and a color as a figure element constituting the appearance of the biological figure.

FIG. 8 is a drawing illustrating a variation of the appearance of the biological figure corresponding to numerical values of the basal metabolic rate according to the embodiment.

As illustrated in FIG. 8, the biological information indicating the basal metabolic rate Me is a biological index that varies a color gradation A of the polyhedron 30 constituting the biological figure. In this embodiment, the biological figure processing units 106 and 204 vary the color of the polyhedron 30 from a green color to a blue color as the numerical value of the basal metabolic rate Me decreases, and vary the color of the polyhedron 30 from the green color to a red color as the numerical value increases.

Thus, coloring the polyhedron 30 in red as the increase of the numerical value of the basal metabolic rate Me provides the measured person watching the biological figure with an impression that he/she has a physical constitution easily burning fat, thus causing him/her to intuitively understand that the basal metabolic rate Me is large. On the other hand, coloring the polyhedron 30 in blue as the decrease of the numerical value of the basal metabolic rate Me provides an impression of having a physical constitution where it is difficult to burn fat, thus causing the measured person to intuitively understand that the basal metabolic rate Me is small.

That is, the variation of the color of the biological figure from the blue to the red as the increase of the numerical value of the basal metabolic rate Me allows the measured person to conceive a degree of the basal metabolic rate Me on the basis of the color itself of the biological figure, so as to intuitively understand the basal metabolic rate Me of himself/herself.

The variation of the color of the biological figure corresponding to the numerical value of the basal metabolic rate Me ensures the measured person to easily recognize the variation of the appearance of the biological figure, so as to easily recognize the difference from the biological figures of others. Accordingly, an impression that the biological figure indicating the health condition of the measured person is unique to only himself/herself is easily provided to the measured person.

Figure 9:
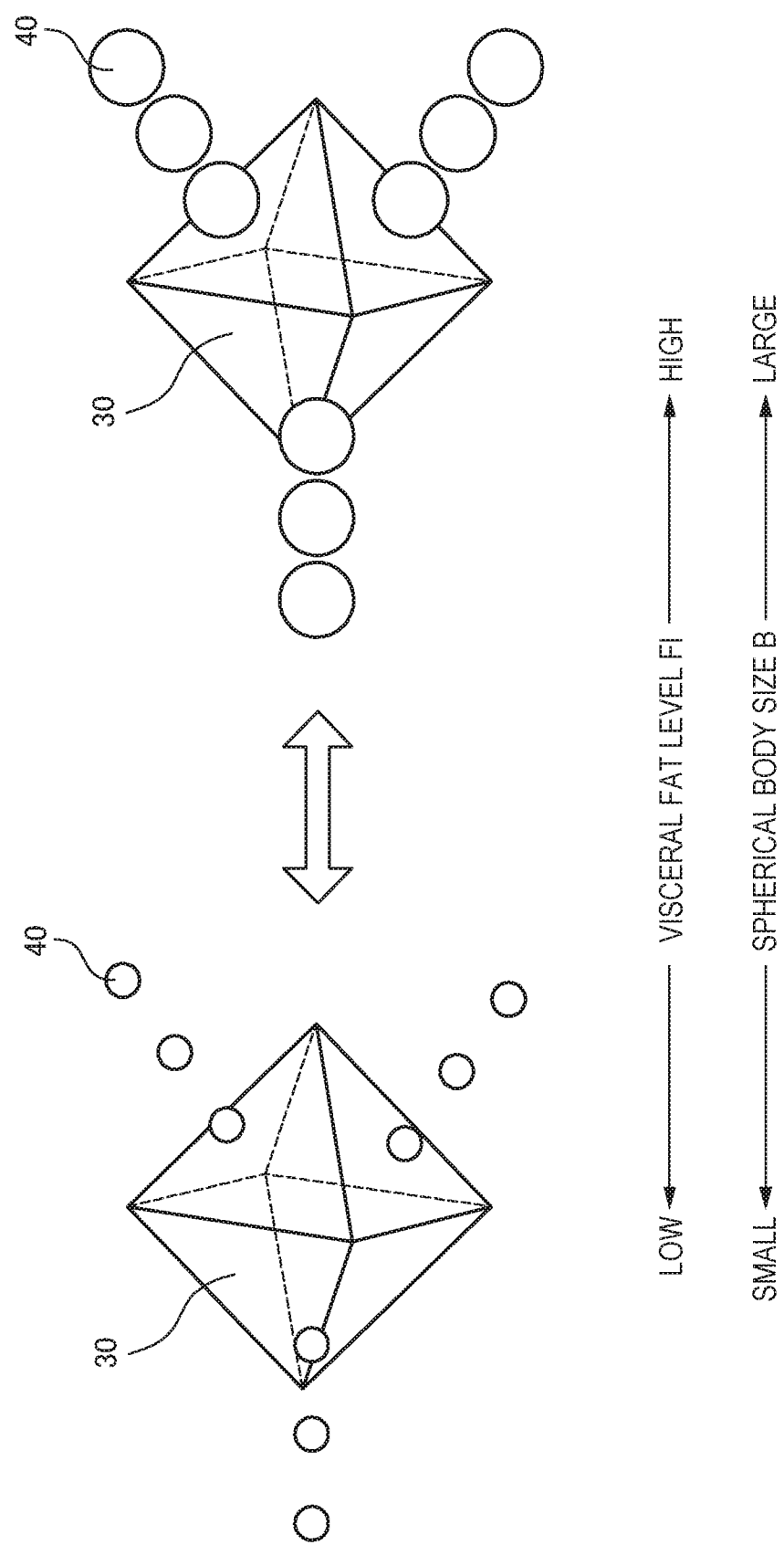
FIG. 9 is a drawing illustrating a relation between a visceral fat level as the biological information and sizes of a plurality of emitted objects as the figure element.

FIG. 9 is a drawing illustrating a variation of the appearance of the biological figure corresponding to a numerical value of the visceral fat level Fl according to the embodiment.

As illustrated in FIG. 9, the biological information indicating the visceral fat level Fl is a biological index that varies sizes B of a predetermined number of white spherical bodies 40 emitted from the center of the polyhedron 30. In this embodiment, the biological figure processing units 106 and 204 decrease diameters of the spherical bodies 40 as the numerical value of the visceral fat level Fl decreases, and increase the diameters of the spherical bodies 40 as the numerical value increases. In such case, the sizes $B_1$ to $B_n$ of the spheres illustrated in FIG. 6 are set so as to increase the size B of the sphere from $B_1$ to $B_n$.

Thus, the variation of the size B of the spherical body 40 corresponding to the visceral fat level Fl also ensures the measured person to easily recognize the variation of the appearance of the biological figure, so as to easily recognize the difference from the biological figures of others. Accordingly, an impression that the biological figure is a distinctive figure indicating the health condition of the measured person himself/herself is easily provided to the measured person. The measured person is ensured to conceive a degree of the visceral fat level Fl on the basis of the size itself of the spherical body 40, so as to intuitively understand the visceral fat level Fl of himself/herself.

While, in this embodiment, a description has been given of the example where the diameter of the spherical body 40 is varied, the present invention is not limited to this embodiment. For example, the number of the spherical bodies 40 may be increased, and the number of the spherical bodies 40 may be increased only in the case where the diameters of a predetermined number of the spherical bodies 40 exceed a predetermined threshold value.

While, in this embodiment, the diameter of the spherical body 40 after emitted from the polyhedron 30 is not changed, the size B of the spherical body 40 may be gradually decreased as the spherical body 40 moves away from the surface of the polyhedron 30. Alternatively, a color of the spherical body 40 may be changed corresponding to the numerical value of the visceral fat level Fl, for example, a degree of transparency of white of the spherical body 40 is increased as the numerical value of the visceral fat level Fl decreases, and the degree of transparency of white of the spherical body 40 is decreased as the numerical value increases.

Furthermore, while, in this embodiment, the plurality of the spherical bodies 40 are emitted from the inside of the polyhedron 30, the plurality of the spherical bodies 40 may be attached by half on the surfaces of the polyhedron 30 without emitting the spherical bodies 40. In this case, the surface on which the spherical body 40 is attached in a plurality of surfaces constituting the polyhedron 30 may be changed to the other surface corresponding to the numerical value of the visceral fat level Fl.

Figure 10:
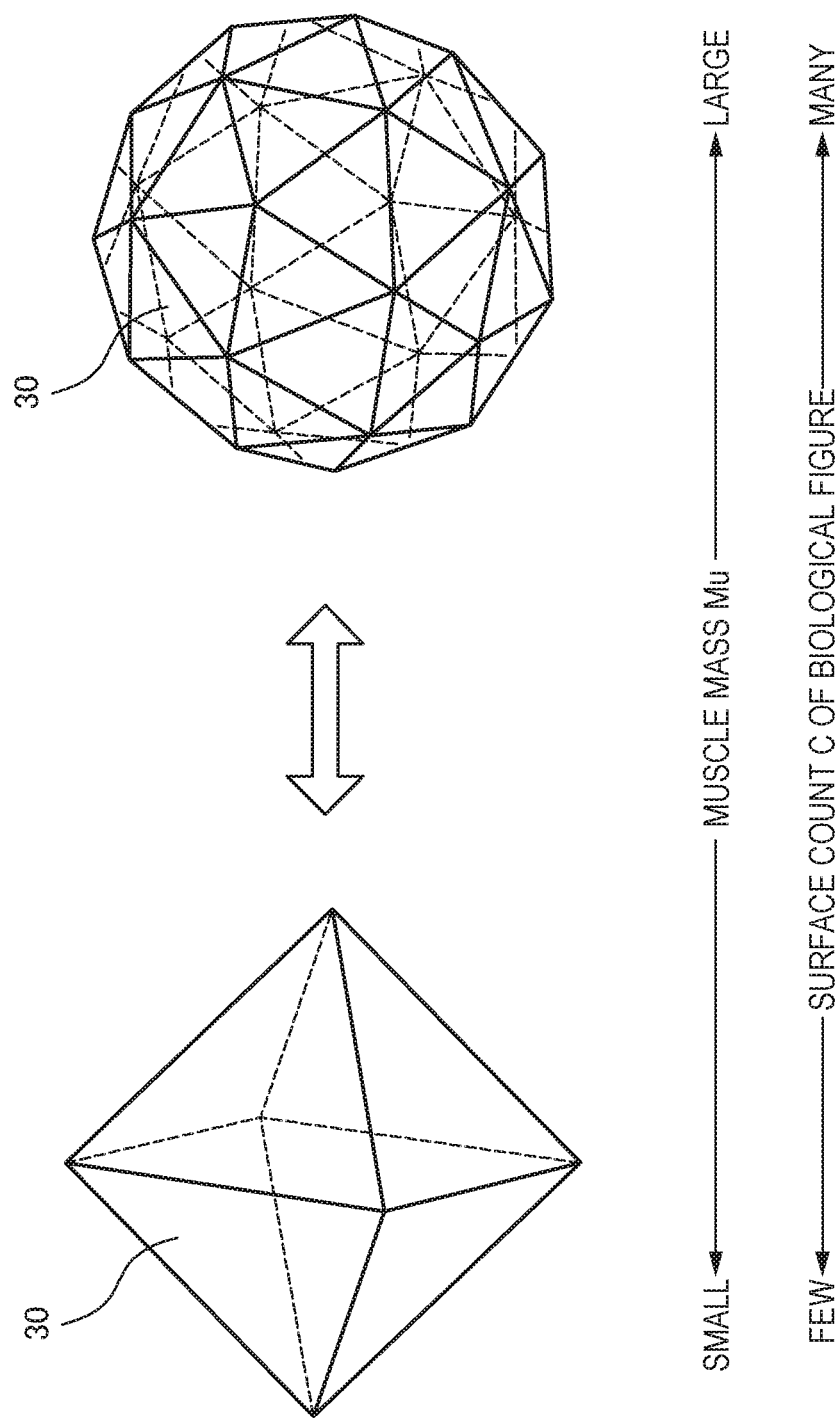
FIG. 10 is a drawing illustrating a relation between a muscle mass as the biological information and the number of surfaces as the figure element.

FIG. 10 is a drawing illustrating a variation of the appearance of the biological figure corresponding to a numerical value of the muscle mass Mu according to the embodiment.

As illustrated in FIG. 10, the biological information indicating the muscle mass Mu is a biological index that varies a surface count C of the polyhedron 30. In this embodiment, the biological figure processing units 106 and 204 decrease the surface count C of the polyhedron 30 as the numerical value of the muscle mass Mu decreases, and increase the surface count C of the polyhedron 30 as the numerical value increases. Accordingly, the surface counts $C_1$ to $C_n$ illustrated in FIG. 6 are set so as to increase the value of the surface count C from $C_1$ to $C_n$.

Thus, the variation of the surface count C of the polyhedron 30 corresponding to the muscle mass Mu also varies the entire outer shape of the biological figure to make the difference from the biological figures of others easily recognized, thus easily providing the measured person with an impression that the biological figure is unique to indicate the health condition of only himself/herself. Furthermore, since the surface count C of the polyhedron 30 increases as the numerical value of the muscle mass Mu increases, a shape of the biological figure is complicated, thus easily generating the biological figure unique to only the measured person.

Specifically, the increase of the surface count C of the polyhedron 30 adds new apexes on specific surfaces and form convex portions on specific surfaces. Then, when the numerical value of the biological information further increases to increase the surface count C, the convex portions further deform so as to complicate the shape of the biological figure. Thus, the deformation of the convex portions formed on the specific surfaces of the polyhedron 30 corresponding to the numerical value of the biological information ensures generating the biological figure in a unique shape.

The biological figure processing units 106 and 204 associating the numerical value of the muscle mass Mu with the surface count C of the polyhedron 30 ensure the measured person to conceive a degree of the muscle mass Mu on the basis of the surface count C of the polyhedron 30, so as to intuitively understand the muscle mass Mu of himself/herself.

Figure 11:
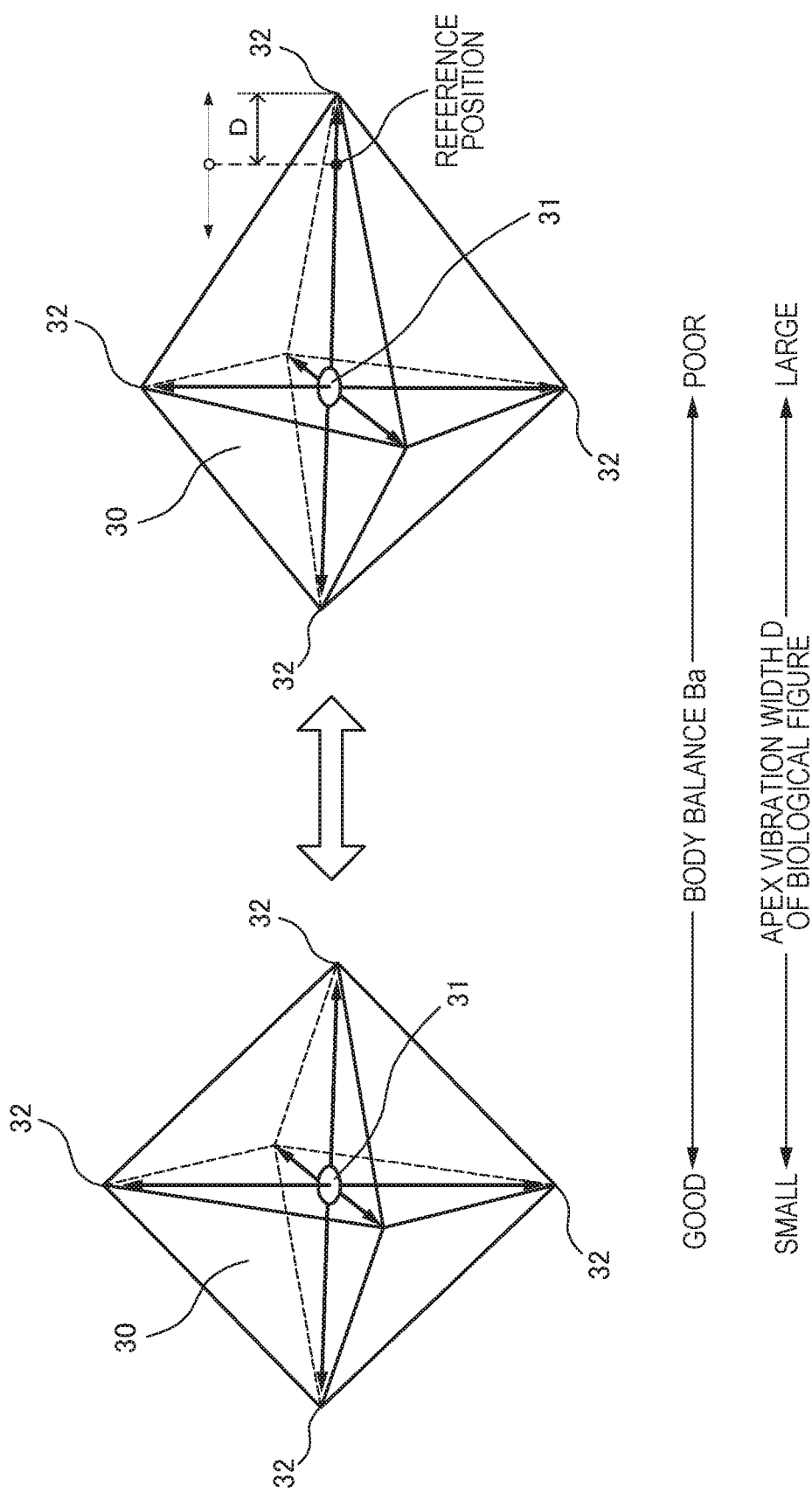
FIG. 11 is a drawing illustrating a relation between a body balance as the biological information and amounts of variation of apexes as the figure element.

FIG. 11 is a drawing illustrating a variation of the appearance of the biological figure corresponding to a numerical value of the body balance according to the embodiment.

As illustrated in FIG. 11, the biological information indicating the body balance Ba is a biological index that varies positions of respective apexes 32 of the polyhedron 30. The body balance Ba of this embodiment possibly has not only a positive value but also a negative value. In the case where the numerical value of the body balance Ba is 0 (zero), the body balance Ba is in a good condition, and as the numerical value moves away from 0, the body balance Ba is indicated to be in a poor condition.

Here, in the case where the numerical value of the body balance Ba is 0, assume that distances from a center point (center of gravity) 31 of the polyhedron 30 to the respective apexes 32 have an identical fixed value, and positions of the apexes are reference positions. Then, the biological figure processing units 106 and 204 decrease a vibration width D of the apex from the reference position as an absolute value of the numerical value of the body balance Ba decreases, and increase the vibration width D of the apex as the absolute value increases. In this case, the vibration width D is set such that the vibration widths $D_1$ to $D_n$ of the apexes illustrated in FIG. 6 decrease to 0 in phases from $D_1$ and increase from 0 in phases to $D_n$.

In this embodiment, the respective apexes 32 constituting the polyhedron 30 vibrate in a predetermined cycle on straight lines connecting the center point 31 to the reference positions by the vibration widths D corresponding to the numerical values of the body balance Ba having the reference positions as the center. The phases of the vibrations of the respective apexes 32 are displaced off one another.

Thus, the variation of the vibration widths of the respective apexes 32 corresponding to the numerical value of the body balance Ba varies the entire outer shape of the biological figure, thus easily providing the measured person with an impression that the biological figure is unique. The vibrations of the respective apexes 32 in the identical cycle regardless of the vibration width D make vibration speeds of the respective apexes 32 high as the increase of the vibration width D, thus ensuring the measured person to easily recognize the difference from the biological figures of others.

Furthermore, displacing the phases of the vibrations of the respective apexes 32 off one another increases unevenness of the polyhedron 30, thus providing the measured person with an impression that the biological figure is distorted as a whole. Accordingly, the measured person is ensured to conceive how poor is the body balance of himself/herself on the basis of the variations of a plurality of the apexes 32, thus intuitively understanding the body balance of himself/herself.

Thus, the variation of a degree of the unevenness formed on the polyhedron 30 corresponding to the numerical value of the biological information ensures generating the biological figure in a unique shape, and ensures the measured person to intuitively understand good or poor of the biological information.

While, in this embodiment, a description has been given of the example where the respective apexes 32 are vibrated by the vibration width D, not limiting to this, the positions of the apexes 32 simply changed such that the shape of the polyhedron 30 is distorted. For example, the biological figure processing units 106 and 204 may freely move the respective apexes 32 from the reference positions without vibrating the respective apexes 32 such that a sum total of distances from positions of the respective apexes 32 to the reference positions becomes the vibration width D.

Alternatively, the biological figure processing units 106 and 204 may move the respective apexes 32 by the vibration widths D in directions perpendicular to directions from the center point 31 to the respective reference positions. Furthermore, the respective apexes 32 may be moved by the vibration widths D at mutually different timings. Accordingly, the unevenness of the polyhedron 30 easily increases and the shape of the polyhedron 30 is easily distorted, thus the unique biological figure can be generated.

Alternatively, the biological figure processing units 106 and 204 may move the position of each apex 32 on a straight line connecting the reference position of each apex 32 to the center point 31 or in a direction perpendicular to the straight line such that a synthesis of displacements from the positions of the respective apexes 32 to the reference positions is 0. While, in this embodiment, a description has been given of the example where every apex constituting the polyhedron 30 is moved, only predetermined apexes among all the apexes may be moved. For example, the biological figure processing units 106 and 204 move only the apexes existing on a horizontal surface passing through the center point 31 and the apexes adjacent to the horizontal surface.

Specific apexes 32 adjacent to one another of the polyhedron 30 may be moved such that one apex 32 is moved in a direction opposite to a moving direction of the other apex 32. This increases the unevenness of the polyhedron 30, thus easily providing an impression that the biological figure is distorted as a whole.

FIG. 12 are drawings describing display images 205B and 205C indicating four biological informations in one biological figure according to the embodiment. The display images 205B and 205C indicate two biological figures B and C whose measurement results are relatively close.

Figure 12B:
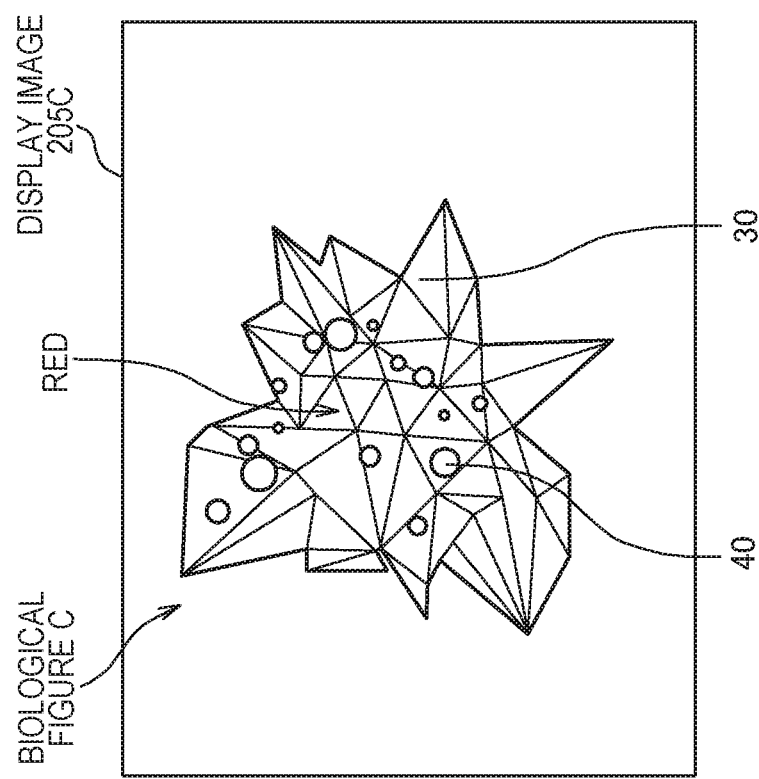
FIG. 12B is a drawing illustrating another exemplary display image of the biological figure according to the embodiment.
Figure 12A:
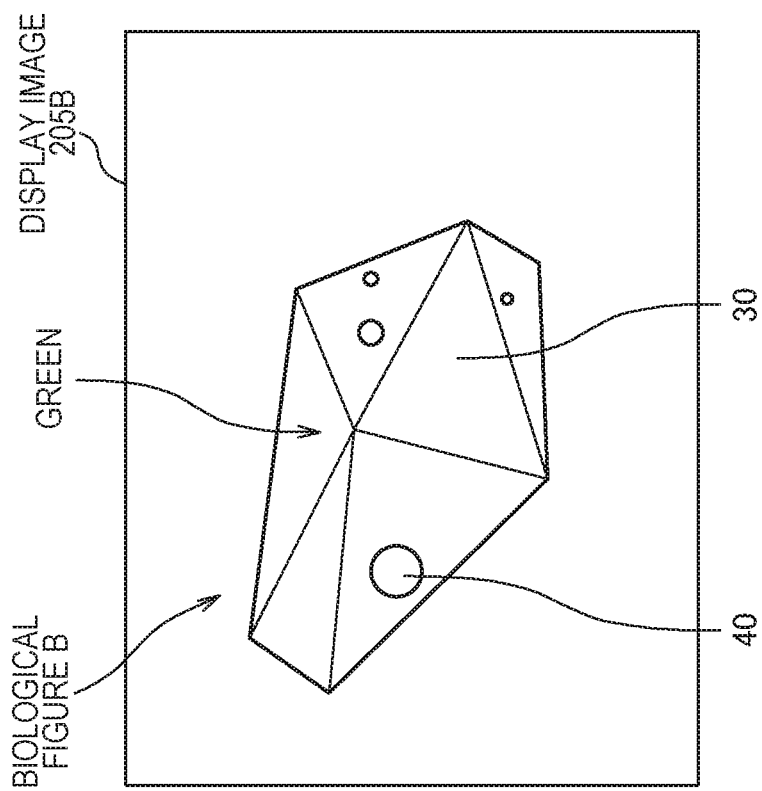
FIG. 12A is a drawing illustrating an exemplary display image of the biological figure according to the embodiment.

As illustrated in FIG. 12A, in the biological figure B, the polyhedron 30 is colored in green, the spherical bodies 40 have relatively large diameters, the surface count of the polyhedron 30 is relatively small, and the distortion of the polyhedron 30 is relatively large. The appearance constituted in this way can provide the measured person with an impression that, for example, the basal metabolic rate Me is moderate, the visceral fat level Fl is high, the muscle mass Mu is small, and the body balance Ba is poor.

On the other hand, as illustrated in FIG. 12B, in the biological figure C, the polyhedron 30 is colored in red, the spherical bodies 40 have moderate diameters, the surface count of the polyhedron 30 is relatively large, and the distortion of the polyhedron 30 is relatively large. The appearance constituted in this way can provide the measured person with an impression that, for example, the basal metabolic rate Me is large, the visceral fat level Fl is moderate, the muscle mass Mu is large, and the body balance Ba is poor.

Thus, indicating the numerical values of the measured biological information by the entire figure ensures the measured person to intuitively understand the measurement result from the total appearance of the biological figure. Furthermore, the measured person does not have to directly watch the numerical value of the visceral fat level and similar value, thus avoiding uncomfortable feeling caused by watching the numerical values. Accordingly, decrease of a positive feeling of the measured person for the measurement of the biological information is reduced.

Reflecting the numerical values of the four biological informations on the respective mutually different figure elements in one biological figure ensures the measured person to intuitively understand a comprehensive evaluation on the health condition of himself/herself from the entire biological figure. In addition, the measured person can understand the degrees or trends of the measurement results of the four biological informations at a glance. It should be noted that the figure elements here mean the specific graphical elements constituting the appearance of the entire figure, for example, the type of the color, the sizes of a plurality of the spherical bodies, the number of all the surfaces, and the displacement amount of the specific apexes, constituting the biological figure.

Furthermore, as seen from a comparison of the biological figure B with the biological figure C, since the biological figure unique to only the measured person himself/herself is indicated to each measured person, the measured person easily feels the measurement of the biological information interesting, thus ensuring increasing the interest in the measurement of the biological information.

<Modification>

While, in this embodiment, a description has been given of the example where the biological figures A to C are indicated on the basis of the biological information calculated by the biological information calculation unit 103 of the biological measurement apparatus 10, the biological figure processing units 106 and 204 may use attribute information of the measured person to change basic tones of the appearances of the biological figures A to C. The attribute information includes, for example, the basic biological information such as the height, the age, and the gender, residence information on a residence of the measured person, time information indicating a time of the measurement by the measured person, or weather information at a measurement time point. The attribute information is simply set by the operating unit 101 and similar unit.

For example, in the case where the gender indicated in the attribute information is female, the size of the polyhedron 30 is slightly decreased, the apex parts of the polyhedron 30 are rounded, the color of the polyhedron 30 is lightened, and the motion of the biological figure is smoothed. On the other hand, in the case where the gender is male, the size of the polyhedron 30 is slightly increased, the unevenness of the polyhedron 30 is increased by a predetermined amount, the color of the polyhedron 30 is darkened, and the motion of the biological figure is made faster to be sharp.

Alternatively, the size of the polyhedron 30 is changed corresponding to the age or the height indicated in the attribute information, and a background color constituting the biological figure is changed corresponding to the residence information of the measured person indicated in the attribute information, for example, changed to white in the Hokkaido area, changed to green in the Chubu area, and changed to blue in the Kyushu area. Instead of this, the background color may be changed to a color easy to conceive an image corresponding to the time information or the weather information at the measurement by the measured person.

Thus, the biological figure processing units 106 and 204 may change the basic tone of the appearance of the biological figure corresponding to the attribute information of the measured person. This ensures easily generating the biological figure having the unique appearance different from one by one, thus causing the measured person to pleasantly perform the measurement of the biological information.

In this embodiment, a description has been given of the example where the control unit 108 causes the storage unit 104 to store the figure conversion table 104A that stores the figure element tables T1 to T4. Then, the biological figure processing unit 106 refers to (associates) the figure element table corresponding to each of the obtained biological informations, and sets the value of the associated figure element to the value corresponding to the numerical value of the biological information. However, the control unit 108 may cause the storage unit 104 not to store the figure conversion table 104A but to store operation expressions for the figure conversion corresponding to the respective biological informations. In this case, the control unit 108 is configured to refer to (associate) the operation expressions for the figure element conversion corresponding to the respective obtained biological informations and use the operation expressions to operate the values of the associated figure elements to set.

As described above, even in the case where the operation expressions for the figure element conversion are used, similarly to the case where the figure conversion tables are used, the step width can be set on the basis of the statistical data on the biological information. For example, as distribution frequency of the normal distribution curve S increases (as approaching the median), the step width is set to a small value, and as the distribution frequency decreases (as approaching the upper limit value or the lower limit value), the step width is set to a large value.

According to the first embodiment of the present invention, the biological figure processing unit 204 of the communication terminal 20 configures the biological information processing device. The biological figure processing unit 204 obtains the biological information indicating the body condition, and associates the different kinds of biological informations to the respective specific graphical elements. Each of the specific graphical elements is the same kind of element that constitutes the appearance of the graphical figure among a plurality of elements constituting the graphical figure. Then, the biological figure processing unit 204 set value depending on the degree of the biological informations for each of the at least one specific graphical element associated with the at least one kind of the obtained biological information, and generates the indicating data of the biological figure that is an aggregate the specific graphical elements on the basis of the set values. It should be noted that the biological figure processing unit 106 of the biological measurement apparatus 10 performs similar process.

Thus, the biological figure processing unit 204 assigns one specific graphical element, such as the type of the color, the plurality of the spherical bodies 40, the number of surfaces constituting the polyhedron 30, and the vibration widths of the plurality of the apexes, constituting the biological figure, to one kind of the biological information. This causes the total appearance of the biological figure to vary corresponding to the numerical values of the biological information, so as to make the difference from the biological figures of others easily recognized, thus providing the measured person with the impression that the biological figure is unique to only himself/herself. Furthermore, indicating the numerical values of the biological information using the biological figure reduces the uncomfortable feeling compared with the case where the measured person directly watches the numerical values of himself/herself.

Therefore, with the embodiment, a variation of one kind of the biological information ensures totally changing the appearance of the biological figure, thus easily indicating features unique to the biological figure indicated to each person corresponding to numerical values of the biological information. Accordingly, the measured person is easily provided with information specific to the person himself/herself as a measurement result, thus ensuring the measured person to be interested in the measurement result of the biological information.

According to the embodiment, the biological figure processing unit 204 associates an outer-shape element with the biological information. The outer-shape element is, for example, the surface count C of the polyhedron 30 and the vibration width D of the apex, one kind of element constituting the outer shape of the biological figure in specific graphical elements constituting the appearance of the biological figure. The biological figure processing unit 204 is configured to set the mutually different values, which correspond to the numerical values of the respective kinds of biological information corresponding to the outer-shape elements, to the outer-shape elements, thus changes the outer shape of the biological figure in phases. This ensures providing the measured person with the unique biological figure different from the biological figures of others, and allows the measured person to determine whether the numerical values of the biological information of himself/herself are good or poor.

According to the embodiment, the biological figure processing unit 204 increases the variation amount of the value set to the specific graphical element to the variation amount of the numerical value of the biological information as the numerical value of the biological information approaches a specific value. This increases a degree of variation of the biological figure as the numerical value of the biological information approaches the specific value. Accordingly, setting the specific value for each kind of the biological information such as the basal metabolic rate and the visceral fat level, which are aimed to cause the measured person and similar person to recognize, relatively largely changes the appearance of the biological figure even if a difference between the specific value and the numerical value of the biological information of the measured person is relatively small in the case where the numerical value of the biological information of the measured person is different at the proximity of the specific value.

For example, since the degree of the variation of the appearance of the biological figure can be increased at the proximity of the specific value where the frequency of occurrence of the numerical value of the biological information increases, the biological figure having the appearance different by each measured person is easily generated in the range of the numerical value where the numerical values of the biological information easily concentrate. The specific value includes, for example, the median, the average value, or the mode of the distribution of the number of people to the numerical values of the biological information.

According to the embodiment, as illustrated in FIG. 7, the predetermined step width that indicates the range of the numerical value of the biological information is determined on the basis of the statistical data on the biological information. The biological figure processing unit 204 changes the values set to the specific graphical element for respective predetermined step widths depending on the degrees of the biological informations. Using the statistical data specifies the section where the numerical values of the biological information easily concentrate, thus ensuring decreasing the step widths in the section. Accordingly, even in the section where the numerical values of the biological information easily concentrate, the appearance of the biological figure can be changed.

According to the embodiment, as illustrated in FIG. 7, the step width is set to the small value as the biological information approaches the median or the average value of the statistical distribution. This reduces a probability where the identical biological figures are generated compared with the case where the step widths of the respective sections are set to be identical. Accordingly, the indication of the identical biological figure to each measured person is reduced.

According to the embodiment, the type of the color, the surface count, the displacement amount of the apex of the polyhedron 30, or the plurality of emitted objects emitted from the polyhedron 30 are used as the specific graphical elements constituting the appearance of the biological figure. Changing the numerical values of such specific graphical element changes the total appearance of the biological figure so as to make the difference from the biological figures of others easily recognized, thus providing the measured person with the impression that the biological figure is unique to only himself/herself.

It should be noted that, the displacement amount of the apex of the polyhedron 30 may be the vibration width of the apex 32 as illustrated in FIG. 11, or may be a displacement amount where the apex 32 is simply moved from the reference position without vibrating the apex 32. Lengths of respective sides constituting the polyhedron 30 may be employed as the specific graphical elements. Even in this case, changing the lengths of the respective sides allows the total appearance of the biological figure to be changed. The plurality of the emitted objects emitted from the polyhedron 30 include, for example, the spherical bodies 40, cubes, or conical bodies.

According to the embodiment, as illustrated in FIG. 6, the different kinds of the biological informations are the basal metabolic rate Me, the visceral fat level Fl, the muscle mass Mu, and the body balance Ba of the body. The specific graphical elements forming the total appearance of the biological figure are the color type including the color gradation A, the surface count C, the vibration width D of the apex of the polyhedron 30, and the sizes B of the plurality of the spherical bodies 40 emitted from the polyhedron 30. The biological figure processing unit 204 associates the basal metabolic rate Me with the color type of the polyhedron 30, associates the visceral fat level Fl with the size B of the spherical bodies 40, associates the muscle mass Mu with the surface count C of the polyhedron 30, and associates the body balance Ba with the vibration width D of the apex of the polyhedron 30.

Thus, reflecting the respective numerical values of the four kinds of the biological information on the mutually different specific graphical elements in one biological figure ensures the measured person to intuitively understand the comprehensive evaluation on the health condition of himself/herself from the appearance of the entire biological figure as illustrated in FIG. 3 and FIG. 12.

According to the embodiment, as illustrated in FIG. 6, the figure conversion information storage unit 203 stores the figure element tables T1 to T4, where the numerical values of the biological information are associated with the values set to the specific graphical elements, for each kind of the biological information. After obtaining the biological information, the biological figure processing unit 204 refers to the figure element tables T1 to T4 stored in the figure conversion information storage unit 203 to identify the figure element table corresponding to the obtained biological information in the figure element tables T1 to T4. The biological figure processing unit 204 sets the values associated with the numerical values of the obtained biological information to the specific graphical element on the basis of the specified figure element table.

Thus, use of the figure element tables T1 to T4 for each kind of the biological information ensures converting the biological information into the biological figure while reducing an operation load compared with the case where the operation expression is used to operate the values of the figure element.

Second Embodiment

Next, a description will be given of an operation of a biological figure processing unit 204 in a second embodiment of the present invention. This embodiment is different from the first embodiment at the point where the display unit 205 displays components of the biological figure before indicating the biological figure.

Figure 13:
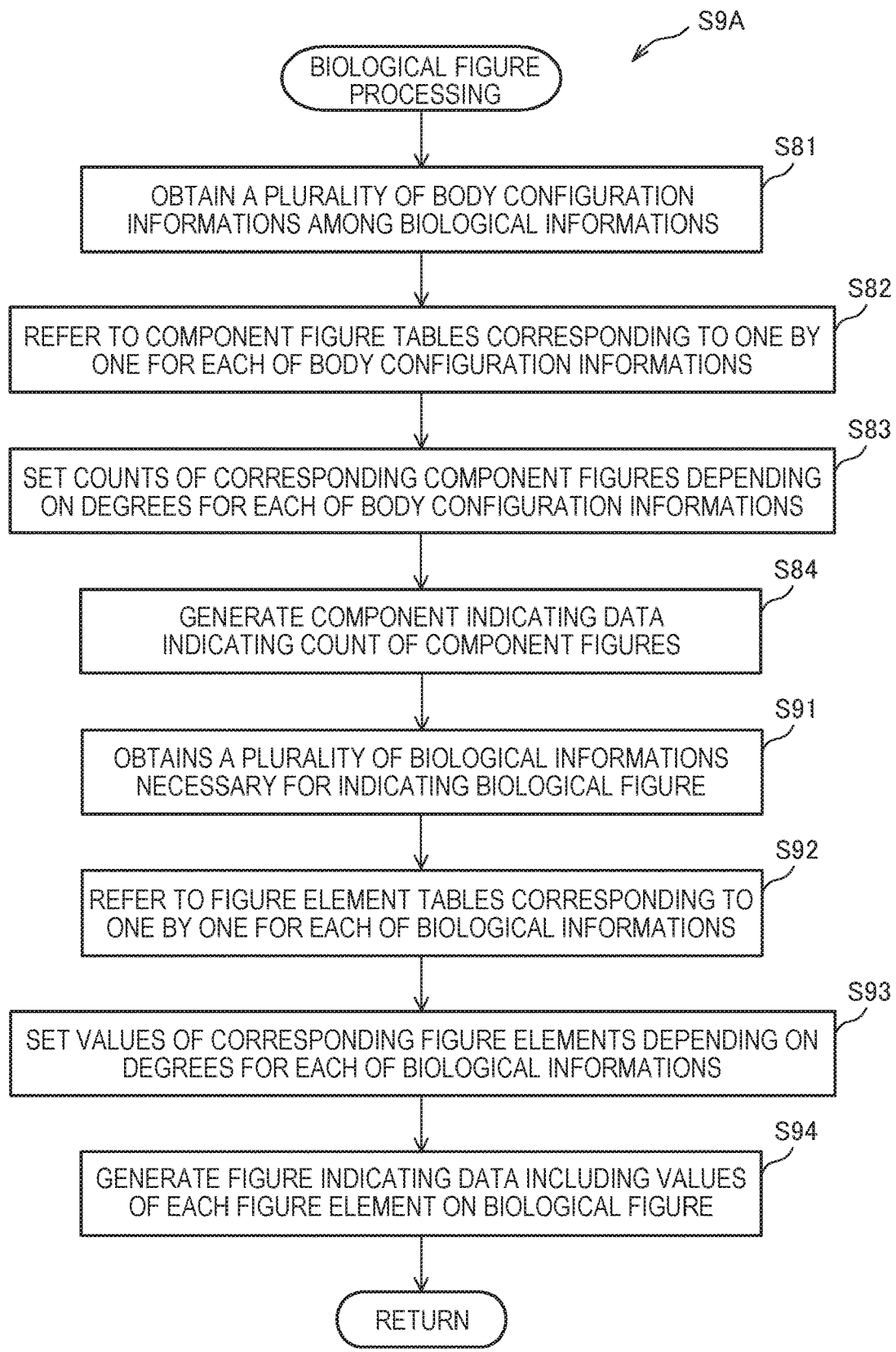
FIG. 13 is a flowchart indicating an exemplary procedure of a biological figure processing in a second embodiment of the present invention.

FIG. 13 is a flowchart indicating an exemplary procedure of a biological figure processing in the second embodiment of the present invention.

The biological figure processing unit 204 according to the embodiment executes the biological figure processing of Step S9A instead of the biological figure processing of Step S9 indicated in FIG. 4. The biological figure processing of Step S9A includes processes of Steps S81 to S84 in addition to the processes of Steps S91 to S94 indicated in FIG. 4. Here, a description will be given of only the processes of Steps S81 to S84 in detail.

In Step S81, the biological figure processing unit 204 obtains a plurality of body configuration informations that indicate component amounts of body components in the biological informations stored in the figure conversion information storage unit 203. That is, the biological figure processing unit 204 obtains the body configuration information indicating the body component.

The biological information stored in the figure conversion information storage unit 203 is the biological information transmitted from the transmitter 105 of the biological measurement apparatus 10. The plurality of body configuration informations obtained by the biological figure processing unit 204 are the fat mass, the muscle mass, the bone mass, and the water content.

In the body configuration information, the fat mass means a whole-body fat mass, and correlates with the height, the weight, the age, and the biological impedance. The muscle mass is also used for indicating the biological figure. The bone mass is an amount of mineral such as calcium contained in the whole bone, and correlates with the fat-free mass. The water content is an amount of moisture such as blood, lymph fluid, intercellular fluid, and visceral fluid, contained in the body, and correlates with the height, the weight, the age, and the biological impedance.

In Step S82, the biological figure processing unit 204 obtains a component figure conversion table from the figure conversion information storage unit 203, the component figure conversion table is a table where component figure tables for generating figures to conceive each kind of the body configuration information are associated with the respective body configuration informations one by one. The biological figure processing unit 204 refers to the component figure tables associated with the respective kinds of the body configuration information in the obtained component figure conversion table. That is, the biological figure processing unit 106 associates the different kind of the body configuration information with respective component figures to conceive each kind of the body configuration information. The component figure conversion table will be described later with reference to the next drawing.

In Step S83, the biological figure processing unit 204 changes the number of the component figures associated with the body configuration information corresponding to the numerical value of the body configuration information for each of the body configuration informations. That is, the biological figure processing unit 204 changes the number of the component figures depending on the degree of the obtained body configuration information.

In Step S84, the biological figure processing unit 204 generates component indicating data that indicates the numbers of the component figures corresponding to four body configuration informations. Then, the biological figure processing unit 204 proceeds to the process of Step S91 described in FIG. 5.

FIG. 14 is a conceptual drawing illustrating an exemplary component figure conversion table 203A stored in the figure conversion information storage unit 203.

The component figure conversion table 203A includes component figure tables T11 to T14 corresponding to the four kinds of the body configuration information. In each of the component figure tables T11 to T14, one kind of the body configuration information is associated with the number of the component figures to conceive the body configuration information, and the number of the component figures increases or decreases in phases as the numerical value of the body configuration information increases. A step number m is a positive number, and set to 256, for example.

In a first component figure table T11, a fat mass F as one kind of the body configuration information is associated with the number of circles as the component figures, and in a second component figure table T12, a muscle mass Mu is associated with the number of squares. In a third component figure table T13, a bone mass Bo is associated with the number of arrows, and in a fourth component figure table T14, a water content Mo is associated with the number of cloud shapes.

For example, on E to H as the numbers of the component figures, as the numerical values of the body configuration information increase with respect to a median or an average value of statistical data, the numbers of the respective component figures are increased, and as the numerical values decrease, the numbers of the respective component figures are decreased.

Thus, the use of the component figure conversion table 203A to generate the four component indicating data ensures indicating main components of the biological information, necessary for generating the biological figures A to C as illustrated in FIG. 3 and FIG. 12, by figures.

Figure 15:
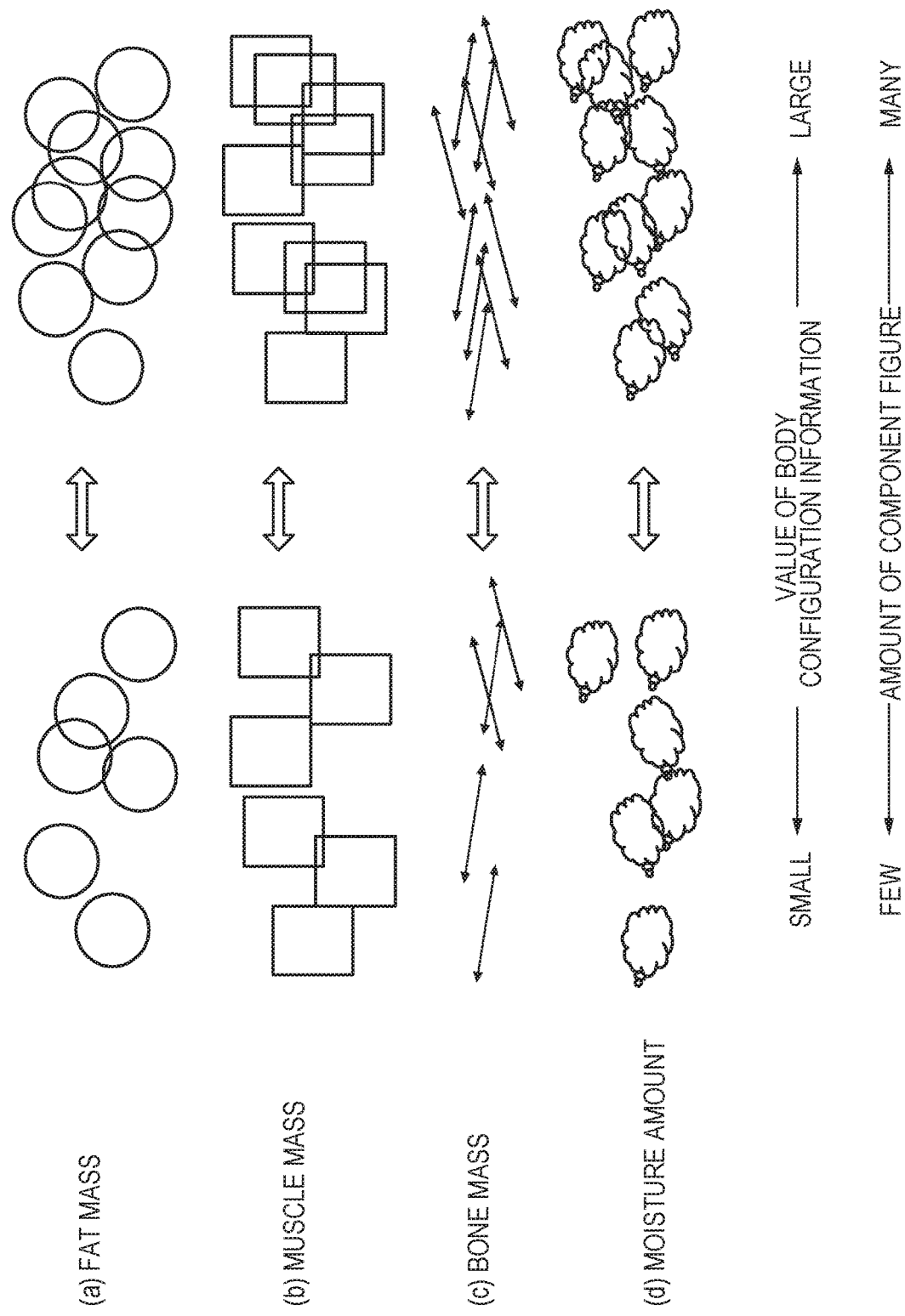
FIG. 15 is a drawing illustrating correspondence of the amount of the component of the body configuration information to the number of the component figures.

FIG. 15 are drawings illustrating correspondence of the numerical value of the body configuration information to the number of the biological figures according to the embodiment.

As illustrated in FIGS. 15(a) to 15(d), the biological figure processing unit 204 increases the numbers of the circles, the squares, the arrows, and the cloud shapes, constituting the component figures, as the numerical values of the four body configuration informations indicating the fat mass F, the muscle mass Mu, the bone mass Bo, and the water content Mo increase, respectively.

Figure 16:
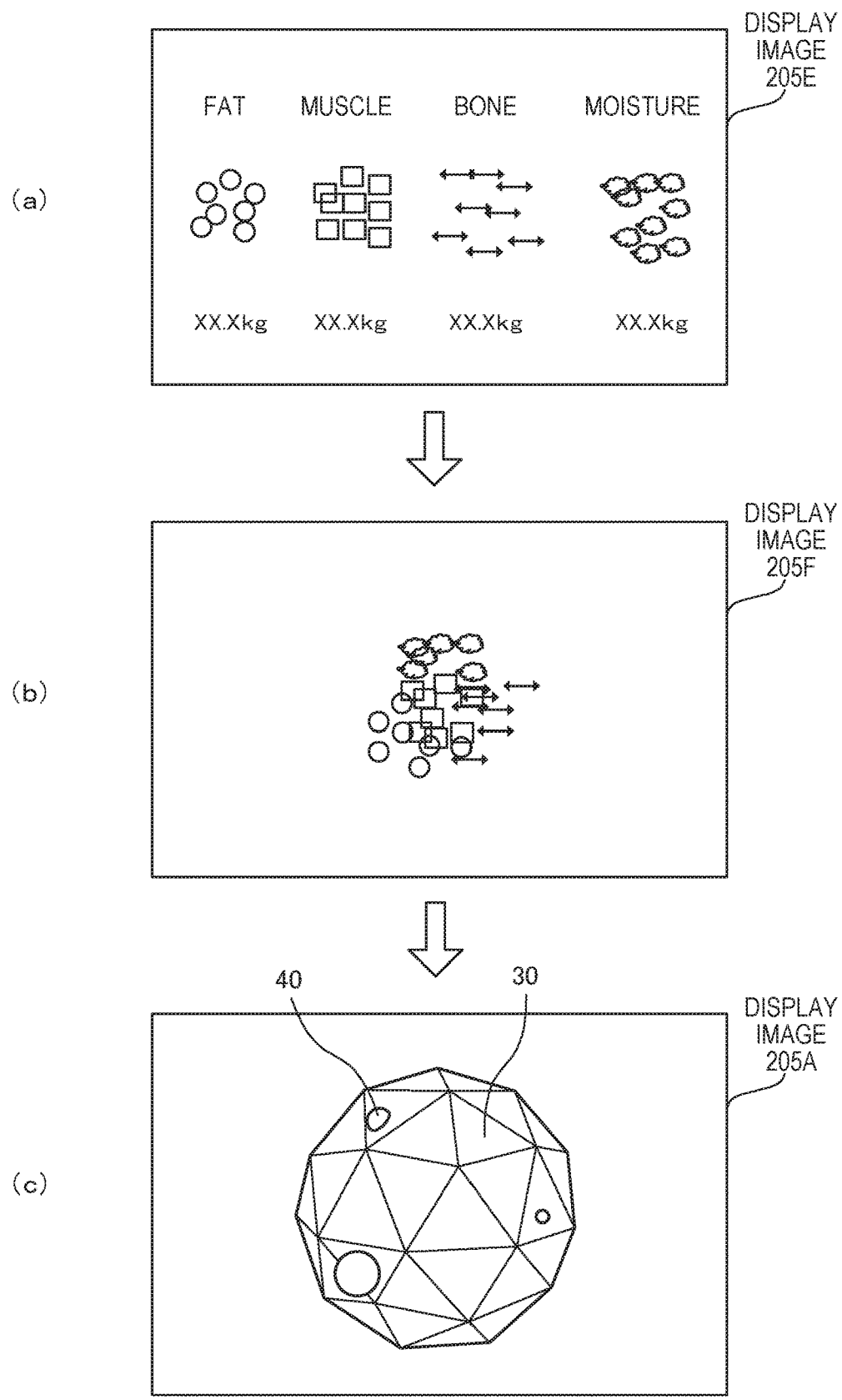
FIG. 16 is a drawing illustrating an exemplary display processing for indicating the component figures according to the embodiment.

FIG. 16 are drawings illustrating an exemplary display method indicating the component figures and the biological figure according to the embodiment.

As illustrated in FIG. 16(a), the display unit 205 generates a display image 205E that displays the component figures of the circle, the square, the arrow, and the cloud shape corresponding to the fat mass F, the muscle mass Mu, the bone mass Bo, and the water content Mo respectively on the basis of the four component indicating data, and displays the display image 205E.

Then, as illustrated in FIG. 16(b), the display unit 205 generates a display image 205F where all the four component figures gathers on the center of the screen, and displays the display image 205F on the screen 21. Subsequently, as illustrated in FIG. 16(c), the display unit 205 displays the display image 205A indicating, for example, the biological figure A illustrated in FIG. 3.

Thus, the display unit 205 displays the four component figures as the components of the biological figure A before indicating the biological figure A. This ensures understanding the components of the biological figure A and causing the measured person to be interested in the biological figure A. Furthermore, the measured person can understand that the surface count of the biological figure A correlates with the muscle mass Mu and the fat mass F correlates with the spherical body 40.

Indicating the number of the component figures as the component of the biological figure A ensures the measured person to intuitively understand whether the numerical value of the body configuration information is large or small with respect to a standard value.

While, in this embodiment, a description has been given of the example where the circle, the square, the arrow, and the cloud shape are used to indicate the fat mass F, the muscle mass Mu, the bone mass Bo, and the water content Mo respectively, the shapes are simply easy to make images of the respective body configuration informations, and not limited to the above shapes.

For example, not only the circle but also a figure including a curved line, for example, a spherical body, may be assigned to the fat mass F, and not only the square but also a figure including a polygon, for example, a cube, may be assigned to the muscle mass Mu. Furthermore, not only the arrow but also a figure where a straight line has spherical both ends or a figure including a straight line like a bone shape may be assigned to the bone mass Bo, and not only the cloud shape but also a figure in an irregular shape such as a water splash, a waterfall, a fountain, a water spray, or a fog may be assigned to the water content Mo.

While, in this embodiment, a description has been given of the example where the number of the component figures are increased as the numerical value of the body configuration information increases, a size (a dimension) of the component figure may be increased as the numerical value of the body configuration information increases.

According to the second embodiment of the present invention, the control unit 206 causes the figure conversion information storage unit 203 to store the component figure conversion table where one kind of the body configuration information is associated with the component figure to conceive the body component. The biological figure processing unit 204 obtains the body configuration information indicating the body component among the biological informations, changes the number or the size of the component figure depending on the degree of the obtained body configuration information, and generates the component indicating data that includes the changed number or size of the component figure. This ensures indicating the numerical value of the body configuration information, which is correlated with the biological information that changes the appearance of the biological figure, by the number of the component figures.

According to the embodiment, the display unit 205 displays the component figures generated on the basis of the component indicating data, and subsequently displays the biological figure. This allows the measured person to easily understand what figure element among the plurality of the figure elements constituting the biological figure corresponds to what kind of the biological information, thus ensuring understanding whether the measurement result is good or poor from the appearance of the biological figure.

Third Embodiment

Next, a description will be given of an operation of a biological figure processing unit 204 in a third embodiment of the present invention. This embodiment is different from the above-described embodiments at the point where the biological figure processing unit 204 displays the biological figures in time series, and displays the number of the component figures discharged from a past biological figure and the number of the component figures absorbed by a latest biological figure.

Figure 17:
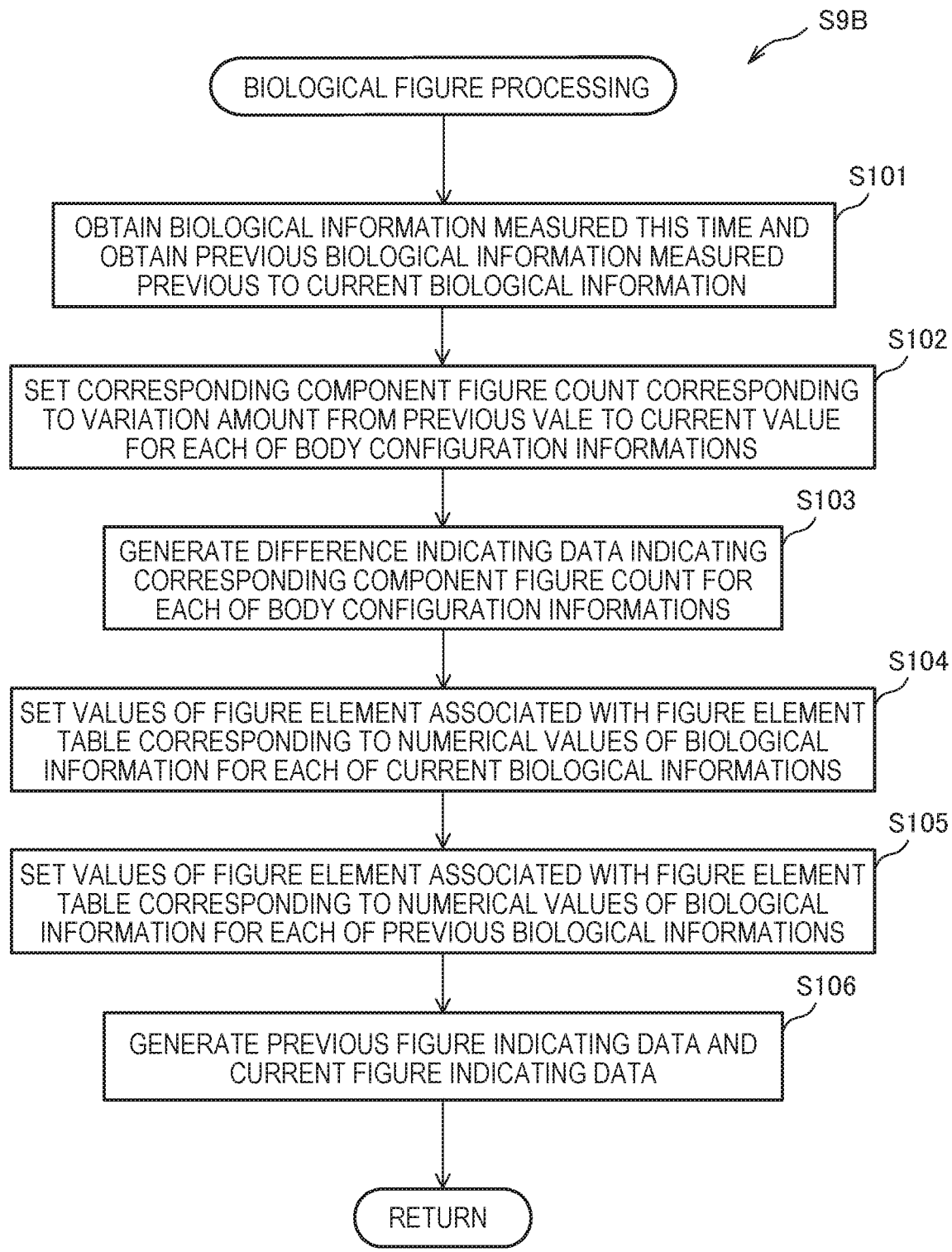
FIG. 17 is a flowchart indicating an exemplary procedure of a biological figure processing in a third embodiment of the present invention.

FIG. 17 is a flowchart indicating an exemplary procedure of a biological figure processing in the third embodiment of the present invention.

In FIG. 17, the biological figure processing unit 204 executes the biological figure processing of Step S9B instead of the biological figure processing of Step S9 indicated in FIG. 4.

In Step S101, the biological figure processing unit 204 obtains current biological information measured by the biological measurement apparatus 10 and previous biological information measured by the biological measurement apparatus 10 previous to the current biological information among the biological informations stored in the figure conversion information storage unit 203. The biological information measured by the biological measurement apparatus 10 includes four biological informations and the four body configuration informations, the basal metabolic rate, the visceral fat level, the muscle mass, and the body balance.

That is, the biological figure processing unit 204 obtains first-time biological information as the previous biological information measured at a first measurement time point, and second-time biological information as the current biological information measured at a second measurement time point after the first measurement time point.

In Step S102, the biological figure processing unit 204 obtains a correspondence table from the figure conversion information storage unit 203, the correspondence table is a table where variation indicating tables indicating absorb/discharge amounts of the component figures between the biological figures whose measurement times are different from one another are associated with the variation amounts of the body configuration informations one by one. Then, the biological figure processing unit 204 obtains a component variation amount from a previous numerical value to a current numerical value, and sets the absorb/discharge amount of the associated component figure to the variation indicating table for each of the body configuration informations.

That is, the biological figure processing unit 204 increases and decreases the number of the component figures associated with the body configuration informations corresponding to a time series difference between the respective body configuration informations in time series included in the previous or the current biological information.

In Step S103, the biological figure processing unit 204 generates difference indicating data that indicates the number of the four component figures. That is, the biological figure processing unit 204 generates the difference indicating data that indicates the number of the component figures corresponding to the time series difference between the two body configuration informations measured at the mutually different time points on the identical body configuration information.

In Step S104, the biological figure processing unit 204 sets the values of the figure elements associated with the figure element tables T1 to T4 illustrated in FIG. 6 corresponding to the numerical values of the biological information for the respective biological informations necessary for generating the biological figure in the current biological information.

In Step S105, the biological figure processing unit 204 sets the values of the figure elements associated with the figure element tables T1 to T4 corresponding to the numerical values of the biological information for the respective biological informations necessary for generating the biological figure in the previous biological information.

In Step S106, the biological figure processing unit 204 generates current figure indicating data that includes the values of the four figure elements set in Step S104 and the time information associated with the current biological information. Furthermore, the biological figure processing unit 204 generates previous figure indicating data that includes the values of the four figure elements set in Step S105 and the time information associated with the previous biological information.

That is, the biological figure processing unit 204 generates first and second indicating data as the previous and current figure indicating data on the basis of the previous and the current biological information, respectively. Then, a sequence of the processes of the biological figure processing in Step S9B terminates.

FIG. 18 is a conceptual drawing illustrating an exemplary correspondence table 203B stored in the figure conversion information storage unit 203.

The correspondence table 203B includes variation indicating tables T21 to T24 corresponding to the component variation amounts of the four body configuration informations. In each of the variation indicating tables T21 to T24, the variation amount of one kind of the body configuration information is associated with a discharge count and an absorb count of the component figure to make an image of the body configuration information. As the component variation amount of the body configuration information increases from 0, the absorb counts $I_{+1}$ to $I_{+k}$ of the component figure increase in phases, and as the component variation amount decreases from 0, the discharge counts $I_{-1}$ to $I_{-k}$ of the component figure increase in phases. A step number k is a positive number, and set to 256, for example.

In a first variation indicating table T21, a fat variation amount Df of the fat mass F as the component variation amount of one kind of the body configuration information is associated with the discharge count and the absorb count of the circles as the component figures. In a second variation indicating table T22, a muscle variation amount Dmu is associated with the discharge count and the absorb count of the squares. In a third variation indicating table T23, a bone variation amount Dbo is associated with the discharge count and the absorb count of the arrows, and in a fourth variation indicating table T24, a moisture variation amount Dmo is associated with the discharge count and the absorb count of the cloud shapes.

Thus, referring to the correspondence table 203B ensures converting the component variation amounts of the four body configuration informations after the previous measurement into the discharge count and the absorb count of the component figure.

Figure 19:
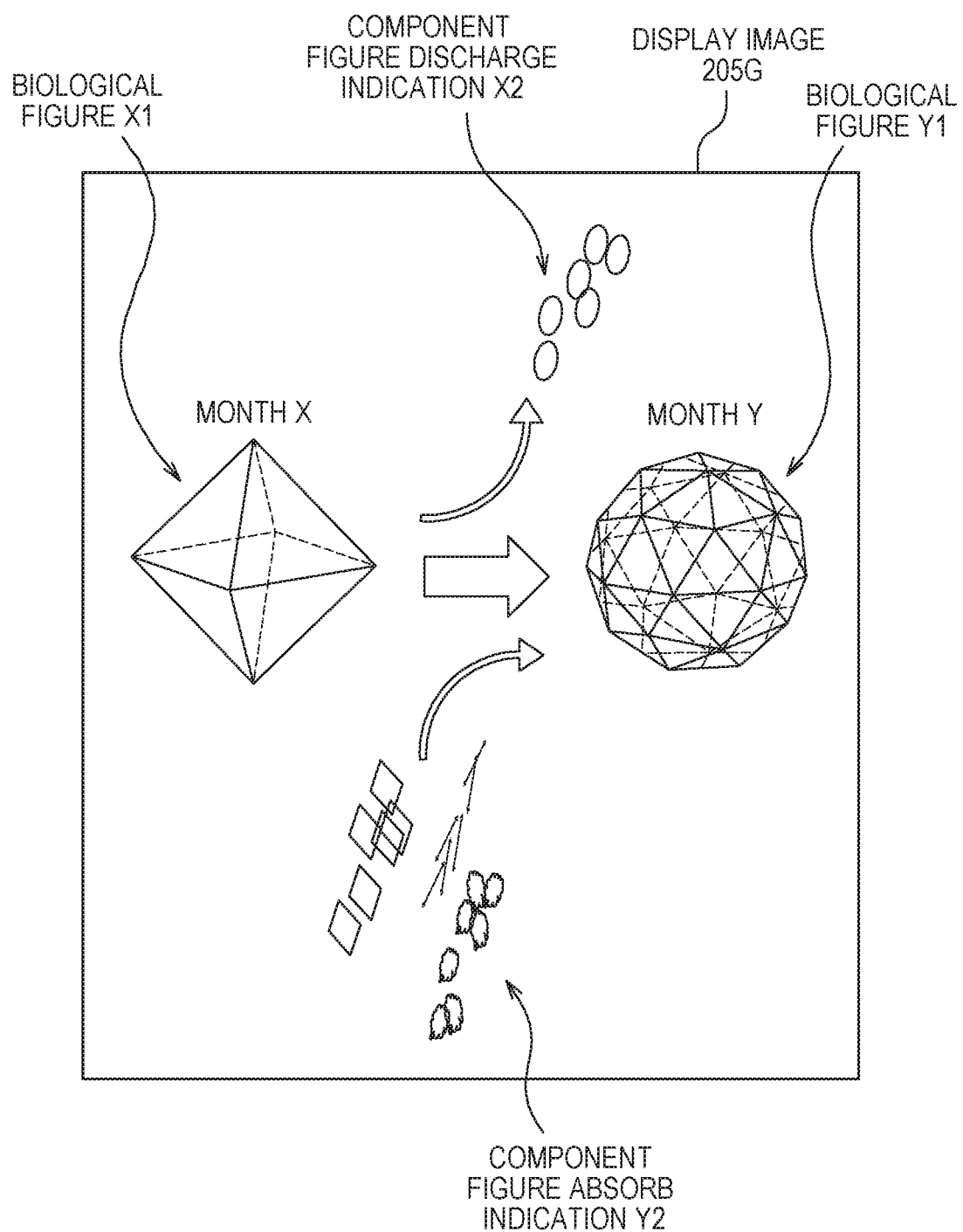
FIG. 19 is a drawing illustrating an exemplary display processing that displays the biological figures in time series and uses the component figures to indicate the variation of the body configuration information.

FIG. 19 is a drawing illustrating an exemplary display method for indicating a transition of the biological figure with the component figures according to the embodiment.

As illustrated in FIG. 19, in a display image 205G, the time information (month X) and a biological figure X1 indicated in the left side are generated on the basis of the previous figure indicating data, and the time information (month Y) and a biological figure Y1 indicated in the right side are generated on the basis of the current figure indicating data.

Furthermore, a component figure discharge indication X2 indicated on the upper side of the display image 205G displays a plurality of the circles as the component figures discharged from the biological figure X1. In the component figure discharge indication X2, the plurality of the circles constituting the biological figure move obliquely upward so as to be discharged from the biological figure X1.

This component figure discharge indication X2 ensures the measured person to recognize that the fat mass F, which is the body configuration information corresponding to the circle, has decreased since the previous measurement. It should be noted that, since the fat mass F has decreased since the previous measurement, the fat variation amount Df indicates a negative value.

On the other hand, a component figure absorb indication Y2 indicated on the lower side of the display image 205G displays a plurality of the three component figures of the squares, the arrows, and the cloud shapes absorbed by a biological figure Y1. In the component figure absorb indication Y2, the plurality of the squares, the arrows, and the cloud shapes constituting the component figures move from the obliquely lower side toward the biological figure Y1 so as to be absorbed by the biological figure Y1.

This component figure absorb indication Y2 ensures the measured person to recognize that the muscle mass Mu, the bone mass Bo, and the water content Mo, which are the body configuration information corresponding to the square, the arrow, and the cloud shape respectively, have increased since the previous measurement. It should be noted that, since the muscle mass Mu, the bone mass Bo, and the water content Mo have increased since the previous measurement, the muscle variation amount Dmu, the bone variation amount Dbo, and the moisture variation amount Dmo indicate positive values.

Thus, the biological figure processing unit 204 determines the component variation amounts of the four body configuration informations whether each positive or negative. When the component variation amount is positive, the biological figure processing unit 204 generates the component figure corresponding to the body configuration information in the component figure absorb indication Y2, and when the component variation amount is negative, the component figure corresponding to the body configuration information is generated in the component figure discharge indication X2.

According to the third embodiment of the present invention, the biological figure processing unit 204 obtains the previous biological information as first indicating biological information that includes the indicating biological information and the body configuration information necessary for indicating the biological figure. Furthermore, the biological figure processing unit 204 obtains the current biological information as second indicating biological information measured after the timing of the measurement of the previous biological information.

Then, the biological figure processing unit 204 increases and decreases the number of the component figures associated with the body configuration information corresponding to the difference between the two body configuration informations included in the previous and current biological information, and generates the difference indicating data that includes the increased/decreased number of the component figures. The biological figure processing unit 204 generates the previous figure indicating data as the first indicating data on the basis of the indicating biological information included in the previous biological information, and generates the current figure indicating data as the second indicating data on the basis of the indicating biological information included in the current biological information.

Accordingly, it is ensured that two biological figures are indicated in time series on the basis of the previous and current figure indicating data, and simultaneously, the numbers of the component figures discharged from the previous biological figure and the component figures absorbed by the current biological figure are indicated on the basis of the difference indicating data.

According to the embodiment, the display unit 205 displays a first biological figure X1 generated on the basis of the previous figure indicating data and a second biological figure Y1 generated on the basis of the current figure indicating data. The display unit 205 further displays the component figure discharge indication X2 where the component figure is an image discharged from the first biological figure X1 and the component figure absorb indication Y2 where the component figure is an image absorbed by the second biological figure Y1 on the basis of the difference indicating data generated in Step S103.

Thus, manners of discharging the component figure and absorbing the component figure in the transition of the biological figure from the first biological figure X1 to the second biological figure Y1 are indicated. This ensures the measured person to understand the body configuration information where the numerical values have been improved, and to have a positive feeling on the measurement of the biological information.

According to the embodiment, the biological figure processing unit 204 obtains the fat mass F, the muscle mass Mu, the bone mass Bo, and the water content Mo of the body as the body configuration information. Then, as illustrated in FIG. 18, the biological figure processing unit 204 associates the fat mass F with a figure including a curved line such as the circle, associates the muscle mass Mu with a figure including a polygon such as the square, associates the bone mass Bo with a figure including a straight line such as the arrow, and associates the water content Mo with a figure in an irregular shape such as the cloud shape.

Thus, converting the body configuration information into the component figure easy to have an image ensures the measured person watching the number of the component figures to intuitively understand the numerical value of the body configuration information of himself/herself, and to have interest in the relation between the biological figure and the component figure. Accordingly, the interest in the measurement of the biological information ensures being increased.

The embodiments of the present invention described above are merely illustration of some application examples of the present invention and not of the nature to limit the technical scope of the present invention to the specific constructions of the above embodiments.

For example, while, in the above embodiment, the color type A, the size B of the spherical body, the surface count C of the polyhedron, and the vibration width D of the apex of the biological figure are employed as the figure elements that changes the total appearance of the biological figure with one kind of the biological information, the present invention is not limited to this. For example, as the figure element, each of a plurality of the sides constituting the polyhedron 30 may be deformed. In this case, for example, curved lines of the respective sides of the polyhedron 30 are enlarged toward outside as the fat mass F increases, and curvatures of the respective sides are increased toward inside when the fat mass F excessively decreases. Even such deformation of the plurality of the sides ensures changing the whole biological figure with one kind of the biological information.

Alternatively, a plurality of holes as the figure elements may be formed on the polyhedron 30. In this case, for example, the number of the holes or the size of each hole formed on the polyhedron 30 is increased as the bone mass Bo decreases to small compared with a predetermined threshold value. Thus, forming a plurality of holes ensures changing the entire shape of the biological figure.

While, in the above embodiment, the figure conversion table illustrated in FIG. 6 is used to associate the biological information with the figure element of the biological figure, for example, one figure element among a plurality of mutually different figure elements may be randomly assigned when the biological figure processing unit 204 obtains the biological information. In this case, for example, the biological figure processing unit 204 associates face image data taken by an imaging device with a figure element assigned to previous biological information to store in the figure conversion information storage unit 203, and associates the previously assigned figure element also with the current biological information on the measured person whose face image data matches. This changes the correspondence relation between the biological information and the figure element for each measured person, thus ensuring indicating the different biological figure to each of the persons to be measured.

While, in the above embodiment, the basal metabolic rate, the visceral fat level, the muscle mass, and the body balance are employed as the biological information used for the biological figure, the biological information such as the weight, the body fat ratio, the bone mass, or a degree of obesity may be employed.

While, in the above embodiment, a three-dimensional solid figure is employed as the biological figure, a two-dimensional figure may be employed. In this case again, similarly to the above embodiment, the biological figure processing unit 204 may color in red as the basal metabolic rate Me increases, increase the number of the apexes of the polygon as the muscle mass Mu increases, increase the number of the circles attached to the polygon as the visceral fat level Fl rises, and increase the vibration width of the apex of the polygon as the body balance Ba becomes poor. Even this case ensures providing the operational advantage similar to the above embodiment.

This application claims priority based on Japanese Patent Application No. 2016-244926, filed with the Japan Patent Office on Dec. 16, 2016, the entire contents of which are incorporated into this specification by reference.

REFERENCE SIGNS LIST

10 biological measurement apparatus (biological information processing device)
20 communication terminal (biological information processing device)
101, 201 operating unit
102 measuring unit
103 biological information calculation unit
104 storage unit (program, associating means, storage means)
105 transmitter
106, 204 biological figure processing unit (obtaining means, associating means, setting means, generating means)
107, 205 display unit (display means)
108, 206 control unit
202 biological information receiver
203 figure conversion information storage unit (program, associating means)
S91 to S94 (obtaining step, associating step, setting step, generating step)

What is claimed is:

1. A biological information processing device comprising a controller programmed to:
    obtain biological information indicating a body condition;
    associate different kinds of the biological information with respective specific graphical elements, each of the respective specific graphical elements constituting a respective specific appearance of a graphical figure, with one of the respective specific graphical elements representing a number of surfaces that constitute a polyhedron which changes in relation to a numerical change in the biological information;
    set value to the specific graphical element depending on degree of the biological information for at least one specific graphical element associated with the biological information obtained; and
    generate indicating data of a biological figure on the basis of the value set, the biological figure being an aggregate of the specific graphical elements, wherein:
    another one of the respective specific graphical element includes a color type and a vibration width of at least one apex of a polyhedron constituting the biological figure, and sizes of a plurality of spherical bodies emitted from a polyhedron in the biological figure, and
    the different kinds of the biological information include a basal metabolic rate, a visceral fat level, a muscle mass, and a body balance of a body.

2. The biological information processing device according to claim 1, wherein:
    the controller is further programmed to set the value to the specific graphical element depending on the degree of the biological information, so as to change an outer shape of the biological figure by changing the number of surfaces that constitute the polyhedron.

3. The biological information processing device according to claim 1, wherein
    the controller is further programmed to increase variation amount of the value set to the specific graphical element with respect to variation amount of numerical value of the biological information as the numerical value of the biological information approaches specific value.

4. The biological information processing device according to claim 3, wherein
    the specific value includes a median, an average value, or a mode of a distribution of a count of people to the numerical value of the biological information.

5. The biological information processing device according to claim 1, wherein:
    the controller is further programmed to set different values to the specific graphical element for each predetermined step width that indicates a range of the numerical value of the biological information, and
    the step width is determined on the basis of statistical data on the biological information.

6. The biological information processing device according to claim 5, wherein:
    the statistical data is a distribution of a count of people to the numerical values of the biological information, and
    the step width is set to a small value as the numerical value of the biological information approaches a median, an average value, or a mode of the distribution.

7. The biological information processing device according to claim 1, wherein
    another one of the respective specific graphical elements includes:
    a color type constituting the biological figure;
    lengths of respective sides, or a displacement amount of at least one apex of the polyhedron constituting the biological figure, or
    a plurality of emitted objects emitted from a main body in the biological figure.

8. The biological information processing device according to claim 1, wherein:
    the controller is further programmed to associate the basal metabolic rate with the color type, associate the visceral fat level with the size of the spherical body, associate the muscle mass with the number of surfaces that constitute the polyhedron, and associate the body balance with the vibration width of the apex.

9. The biological information processing device according to claim 1, wherein:
the controller is further programmed to:
obtain attribute information of a measured person as the biological information; and
change a color, a size, or a basic tone of motion of the biological figure correspondingly to the attribute information.

10. The biological information processing device according to claim 1, further comprising
a storage device that stores figure element tables for each kind of the biological information, the figure element tables being tables where the numerical values of the biological information are associated with the respective values set to the specific graphical element, wherein:
the controller is further programmed to:
specify the figure element table corresponding to the biological information in the figure element tables stored in the storage device when the biological information is obtained; and
set the values associated with the numerical values of the biological information obtained to the specific graphical elements on the basis of the specified figure element table.

11. The biological information processing device according to claim 1, further comprising
a display that displays the biological figure generated on the basis of the indicating data.

12. The biological information processing device according to claim 11, wherein
the controller is further programmed to:
change the displacement amounts of a plurality of the apexes constituting the polyhedron of the biological figure depending on the numerical value of the biological information, and
move the apexes by the displacement amounts at mutually different timings displayed by the display.

13. The biological information processing device according to claim 1, wherein
the biological information includes body configuration information indicating body components,
the controller is further programmed to:
associate different kind of the body configuration information with respective component figures to conceive the body component;
change the counts or the sizes of the component figures depending on degree of the body configuration information obtained; and
generate component indicating data that includes the counts or the sizes of the component figures.

14. The biological information processing device according to claim 13, further comprising
a display that displays the component figures generated on the basis of the component indicating data, and subsequently displays the biological figure.

15. The biological information processing device according to claim 13, wherein
the controller is further programmed to:
obtain first-time biological information and second-time biological information, the first-time biological information being the biological information measured at a first measurement time point, the second-time biological information being the biological information measured at a second measurement time point after the first measurement time point;
increase and decrease the count of the component figures associated with the body configuration information corresponding to a difference between degrees of the body configuration information included in each of the first-time biological information and the second-time biological information;
generate difference indicating data that includes the count of the component figures increased/decreased;
generate first indicating data that indicates a first biological figure on the basis of the first-time biological information; and
generate second indicating data that indicates a second biological figure on the basis of the second-time biological information.

16. The biological information processing device according to claim 15, further comprising
a display that displays the first biological figure on the basis of the first indicating data, and displays the second biological figure on the basis of the second indicating data, wherein
the display displays, on the basis of the difference indicating data, an image where the component figures are discharged from the first biological figure or an image where the component figures are absorbed by the second biological figure.

17. The biological information processing device according to claim 13, wherein
the different kinds of the body configuration information includes a fat mass, a muscle mass, a bone mass, and a water content of a body,
the component figures include a figure including a curved line, a figure including a straight line, a figure including a polygon, and a figure in an irregular shape,
the controller is further programmed to associate the fat mass with the figure including the curved line, associate the muscle mass with the figure including the polygon, associate the bone mass with the figure including the straight line, and associate the water content with the figure in the irregular shape.

18. A non-transitory computer-readable recording medium including a program that causes a computer configured to process biological information to execute:
obtaining biological information indicating a body condition;
associating different kinds of the biological information with respective specific graphical elements, each of the respective specific graphical elements constituting a respective specific appearance of a graphical figure, with one of the respective specific graphical elements representing a number of surfaces that constitute a polyhedron which changes in relation to a numerical change in the biological information;
setting value to the specific graphical element depending on degree of the biological information for at least one specific graphical element associated with the biological information obtained by the obtaining; and
generating indicating data of a biological figure on the basis of the value set by the setting, the biological figure being an aggregate of the specific graphical elements, wherein:
another one of the respective specific graphical element includes a color type and a vibration width of at least one apex of a polyhedron constituting the biological figure, and sizes of a plurality of spherical bodies emitted from a polyhedron in the biological figure, and the different kinds of the biological information include a basal metabolic rate, a visceral fat level, a muscle mass, and a body balance of a body.

19. A biological information processing method comprising:

obtaining biological information indicating a body condition;

associating different kinds of the biological information with respective specific graphical elements, each of the respective specific graphical elements constituting a respective specific appearance of a graphical figure, with one of the respective specific graphical elements representing a number of surfaces that constitute a polyhedron which changes in relation to a numerical change in the biological information;

setting value to the specific graphical element depending on degree of the biological information for at least one specific graphical element associated with the biological information obtained by the obtaining; and generating indicating data of a biological figure on the basis of the value set by the setting, the biological figure being an aggregate of the specific graphical elements, wherein:

another one of the respective specific graphical element includes a color type and a vibration width of at least one apex of a polyhedron constituting the biological figure, and sizes of a plurality of spherical bodies emitted from a polyhedron in the biological figure, and the different kinds of the biological information include a basal metabolic rate, a visceral fat level, a muscle mass, and a body balance of a body.

\* \* \* \* \*